(12) United States Patent
Yang

(10) Patent No.: US 6,878,530 B2
(45) Date of Patent: Apr. 12, 2005

(54) METHODS FOR DETECTING POLYMORPHISMS IN NUCLEIC ACIDS

(75) Inventor: Qinghong Yang, Mountain View, CA (US)

(73) Assignee: Panomics, Inc., Redwood City, CA (US)

( * ) Notice: Subject to any disclaimer, the term of this patent is extended or adjusted under 35 U.S.C. 154(b) by 164 days.

(21) Appl. No.: 10/071,302

(22) Filed: Feb. 7, 2002

(65) Prior Publication Data

US 2003/0154034 A1 Aug. 14, 2003

(51) Int. Cl.⁷ ............................ C12P 19/34; C12Q 1/68; C07H 21/04
(52) U.S. Cl. ......................... 435/91.2; 435/6; 536/23.1; 536/24.2; 536/24.33
(58) Field of Search .................... 435/91.2, 6; 536/23.1, 536/24.2, 24.3, 24.33

(56) References Cited

U.S. PATENT DOCUMENTS

| | | | |
|---|---|---|---|
| 5,698,400 | A | 12/1997 | Cotton et al. |
| 5,824,471 | A | 10/1998 | Mashal et al. |
| 6,013,439 | A | 1/2000 | Lishanski et al. |
| 6,232,104 | B1 * | 5/2001 | Lishanski et al. .......... 435/91.2 |
| 6,653,079 | B2 * | 11/2003 | Yang et al. ..................... 435/6 |

FOREIGN PATENT DOCUMENTS

| WO | WO 97/23646 | 12/1996 |
|---|---|---|
| WO | WO 00/20643 | 10/1999 |

OTHER PUBLICATIONS

Wu et al. (Nucleic Acids Research (1998) vol. 26, pp. 5432–5440).*
Kumar et al (Nucleic Acids Research (1998) vol. 26, pp. 831–838).*
Giesen et al. (Nucleic Acids Research (1998) vol. 26, pp. 5004–5006).*
Zerbib, D., et al., "Coordinated Actions of RuvABC in Holliday Junction Processing," *J. Mol. Biol.*, (1998) vol. 281, No. mb981959, pp. 621–630 (0022–2836/98/340621–10).
Adams, D., et al., "Unwinding of Closed Circular DNA by the *Escherichia coli* RuvA and RuvB Recombination/Repair Proteins," *J. Mol. Biol.* (1995) vol. 247, pp. 404–417 (022/2836/95/130404–14).

Mezard, C., et al., "*Escherichia coli* RuvB$^{L288S}$. a Mutant RuvB Protein That Exhibits Wild–Type Activities in Vitro but Confers a UV–Senstitive ruv Phenotype in Vivo," *Nucleic Acids Research*, (1999) vol. 27, No. 5, pp. 1275–1282 (Imperial Cancer Research Fund).
Panyutin, I., et al., "The Kinetics of Spontaneous DNA Branch Migration," *Proc. Natl. Acad. Sci.*, (1994) vol. 91, pp. 2021–2025 (National Institutes of Health).
PCT/US01/29922, International Search Report, mailed Feb. 13, 2002.
PCT/US01/51104, International Search Report, mailed May 13, 2001.
PCT/US01/07858, International Search Report, mailed Jun. 6, 2001.
Davies et al., "Formation of RuvABC–Holliday Junction Complexes In Vitro," *Current Biology* vol. 8 No. 12, pp. 725–727 (1998).
Panyulin et al., "Formation Of A Single Base Mismatch Impedes Spontaneous DNA Branch Migration," *J Mol Biol.* vol. 230 No. 2, pp. 413–424 (1993).
Saiki et al., "Enzymatic Amplification of β–Globin Genomic Sequences and Restriction Site Analysis For Diagnosis of Sickle Cell Anemia," *Science*, vol. 230(4732) pp. 1350–1354, (1985).
Whitby et al., "Interactions between RuvA and RuvC at Holliday junctions: inhibition of junction cleavage and formation of a RuvA–RuvC–DNA complex," *J Mol Biol* vol. 264(5) pp. 878–890 (1996).

* cited by examiner

*Primary Examiner*—Marjorie Moran
*Assistant Examiner*—Lori A. Clow

(57) ABSTRACT

The present invention provides methods for determining the genotype of a nucleic acid at the site of a polymorphism. The methods achieve sensitivities great enough to detect the presence of any difference between the nucleic acids, even single nucleotide polymorphisms. In the methods, the nucleic acid is compared to a reference nucleic acid having a known genotype. The nucleic acids can be of any length, even less than 100 base pairs. In methods, one or more extra mismatches are introduced into the nucleic acids at or near the site of the polymorphism. The nucleic acids are contacted under conditions in which they are capable of forming a stable four-way complex that can be detected to indicate that the nucleic acids differ in genotype.

Figure 1A:
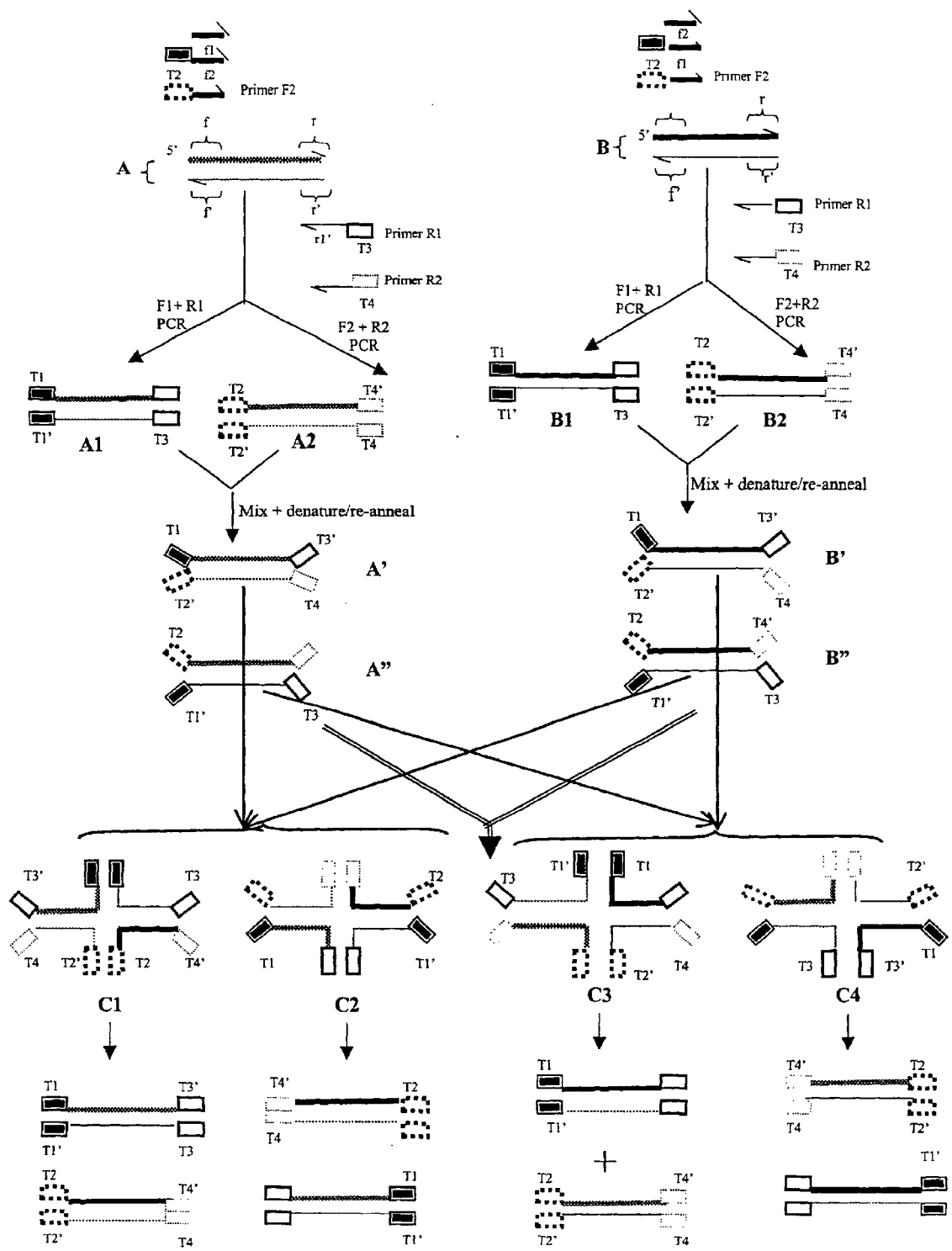

22 Claims, 10 Drawing Sheets a b 69 bp amplicon
5' → SNP 25 bp
3' → SNP 43 bp mm 1+6

67 bp amplicon
5' → SNP 25 bp
3' → SNP 41 bp mm 1+2

SEQUENCE LISTING

<160> NUMBER OF SEQ ID NOS: 43

<210> SEQ ID NO 1
<211> LENGTH: 21
<212> TYPE: DNA
<213> ORGANISM: Artificial Sequence
<220> FEATURE:
<223> OTHER INFORMATION: Description of artificial sequence: forward
      primer

<400> SEQUENCE: 1
cacttggcag atttgaagag c                                             21

<210> SEQ ID NO 2
<211> LENGTH: 25
<212> TYPE: DNA
<213> ORGANISM: Artificial Sequence
<220> FEATURE:
<223> OTHER INFORMATION: Description of artificial sequence: forward
      primer

<400> SEQUENCE: 2
aaatagtaga aagcgtgaga gcact                                         25

<210> SEQ ID NO 3
<211> LENGTH: 32
<212> TYPE: DNA
<213> ORGANISM: Artificial Sequence
<220> FEATURE:
<223> OTHER INFORMATION: Description of artificial sequence: forward
      primer
<220> FEATURE:
<221> NAME/KEY: misc_feature
<222> LOCATION: (26)..(26)
<223> OTHER INFORMATION: n= a or t

<400> SEQUENCE: 3
aaatagtaga aagcgtgaga gcactnttag ga                                 32

```
<210> SEQ ID NO 4
<211> LENGTH: 32
<212> TYPE: DNA
<213> ORGANISM: Artificial Sequence
<220> FEATURE:
<223> OTHER INFORMATION: Description of artificial sequence: forward
      primer
<220> FEATURE:
<221> NAME/KEY: misc_feature
<222> LOCATION: (26)..(26)
<223> OTHER INFORMATION: n= c or t

<400> SEQUENCE: 4
aaatagtaga aagcgtgaga gcactnttag ga                                    32

<210> SEQ ID NO 5
<211> LENGTH: 32
<212> TYPE: DNA
<213> ORGANISM: Artificial Sequence
<220> FEATURE:
<223> OTHER INFORMATION: Description of artificial sequence: forward
      primer
<220> FEATURE:
<221> NAME/KEY: misc_feature
<222> LOCATION: (26)..(26)
<223> OTHER INFORMATION: n= a or c

<400> SEQUENCE: 5
aaatagtaga aagcgtgaga gcactnttag ga                                    32

<210> SEQ ID NO 6
<211> LENGTH: 32
<212> TYPE: DNA
<213> ORGANISM: Artificial Sequence
<220> FEATURE:
<223> OTHER INFORMATION: Description of artificial sequence: forward
      primer
<220> FEATURE:
<221> NAME/KEY: misc_feature
<222> LOCATION: (26)..(26)
<223> OTHER INFORMATION: n= t or g

<400> SEQUENCE: 6
aaatagtaga aagcgtgaga gcactnttag ga                                    32

<210> SEQ ID NO 7
<211> LENGTH: 32
<212> TYPE: DNA
<213> ORGANISM: Artificial Sequence
<220> FEATURE:
<223> OTHER INFORMATION: Description of artificial sequence: forward
      primer
<220> FEATURE:
<221> NAME/KEY: misc_feature
<222> LOCATION: (26)..(26)
<223> OTHER INFORMATION: n= a or g

<400> SEQUENCE: 7
aaatagtaga aagcgtgaga gcactnttag ga                                    32

<210> SEQ ID NO 8
<211> LENGTH: 27
<212> TYPE: DNA
<213> ORGANISM: Artificial Sequence
<220> FEATURE:
<223> OTHER INFORMATION: Description of artificial sequence: forward
      primer

<400> SEQUENCE: 8
gcaaatagta gaaagcgtga gagcact                                          27
```

<210> SEQ ID NO 9
<211> LENGTH: 29
<212> TYPE: DNA
<213> ORGANISM: Artificial Sequence
<220> FEATURE:
<223> OTHER INFORMATION: Description of artificial sequence: forward
      primer

<400> SEQUENCE: 9
aagcaaatag tagaaagcgt gagagcact                                    29

<210> SEQ ID NO 10
<211> LENGTH: 31
<212> TYPE: DNA
<213> ORGANISM: Artificial Sequence
<220> FEATURE:
<223> OTHER INFORMATION: Description of artificial sequence: forward
      primer

<400> SEQUENCE: 10
ggaagcaaat agtagaaagc gtgagagcac t                                 31

<210> SEQ ID NO 11
<211> LENGTH: 33
<212> TYPE: DNA
<213> ORGANISM: Artificial Sequence
<220> FEATURE:
<223> OTHER INFORMATION: Description of artificial sequence: forward
      primer

<400> SEQUENCE: 11
gaggaagcaa atagtagaaa gcgtgagagc act                               33

<210> SEQ ID NO 12
<211> LENGTH: 35
<212> TYPE: DNA
<213> ORGANISM: Artificial Sequence
<220> FEATURE:
<223> OTHER INFORMATION: Description of artificial sequence: forward
      primer

<400> SEQUENCE: 12
aagaggaagc aaatagtaga aagcgtgaga gcact                             35

<210> SEQ ID NO 13
<211> LENGTH: 32
<212> TYPE: DNA
<213> ORGANISM: Artificial Sequence
<220> FEATURE:
<223> OTHER INFORMATION: Description of artificial sequence: forward
      primer

<400> SEQUENCE: 13
aaatagtaga aagcgtgaga gcactattag ga                                32

<210> SEQ ID NO 14
<211> LENGTH: 32
<212> TYPE: DNA
<213> ORGANISM: Artificial Sequence
<220> FEATURE:
<223> OTHER INFORMATION: Description of artificial sequence: forward
      primer

<400> SEQUENCE: 14
aaatagtaga aagcgtgaga gcactttag ga                                 32

```
<210> SEQ ID NO 15
<211> LENGTH: 32
<212> TYPE: DNA
<213> ORGANISM: Artificial Sequence
<220> FEATURE:
<223> OTHER INFORMATION: Description of artificial sequence: forward
      primer

<400> SEQUENCE: 15
aaatagtaga aagcgtgaga gcactgttag ga                              32

<210> SEQ ID NO 16
<211> LENGTH: 32
<212> TYPE: DNA
<213> ORGANISM: Artificial Sequence
<220> FEATURE:
<223> OTHER INFORMATION: Description of artificial sequence: forward
      primer

<400> SEQUENCE: 16
aaatagtaga aagcgtgaga gcactcttag ga                              32

<210> SEQ ID NO 17
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 17
aaatagtaga aagcgtgaga gcacaattag                                 30

<210> SEQ ID NO 18
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 18
aaatagtaga aagcgtgaga gcacagttag                                 30

<210> SEQ ID NO 19
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 19
aaatagtaga aagcgtgagt gcacaattag                                 30

<210> SEQ ID NO 20
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 20
aaatagtaga aagcgtgagt gcacagttag                                 30
```

<210> SEQ ID NO 21
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 21
aaatagtaga aagcgagaga gcacaattag                    30

<210> SEQ ID NO 22
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 22
aaatagtaga aagcgagaga gcacagttag                    30

<210> SEQ ID NO 23
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 23
aaatagtaga atgcgtgaga gcacaattag                    30

<210> SEQ ID NO 24
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 24
aaatagtaga atgcgtgaga gcacagttag                    30

<210> SEQ ID NO 25
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 25
aaatagttga aagcgtgaga gcacaattag                    30

<210> SEQ ID NO 26
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 26
aaatagttga aagcgtgaga gcacagttag                    30

<210> SEQ ID NO 27

```
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 27
aaatagtaga aagcgtgaga gcacaaatag                                    30

<210> SEQ ID NO 28
<211> LENGTH: 30
<212> TYPE: DNA
<213> ORGANISM: Artificial Sequence
<220> FEATURE:
<223> OTHER INFORMATION: Description of artificial sequence: forward
      primer

<400> SEQUENCE: 28
aaatagtaga aagcgtgaga gcacagatag                                    30

<210> SEQ ID NO 29
<211> LENGTH: 42
<212> TYPE: DNA
<213> ORGANISM: Artificial Sequence
<220> FEATURE:
<223> OTHER INFORMATION: Description of artificial sequence: reverse
      tailed primer

<400> SEQUENCE: 29
accatgctcg agattacgag tcacaaatta cgtgagaaac cg                      42

<210> SEQ ID NO 30
<211> LENGTH: 42
<212> TYPE: DNA
<213> ORGANISM: Artificial Sequence
<220> FEATURE:
<223> OTHER INFORMATION: Description of artificial sequence: reverse
      tailed primer

<400> SEQUENCE: 30
gatcctaggc ctcacgtatt tcacaaatta cgtgagaaac cg                      42

<210> SEQ ID NO 31
<211> LENGTH: 41
<212> TYPE: DNA
<213> ORGANISM: Artificial Sequence
<220> FEATURE:
<223> OTHER INFORMATION: Description of artificial sequence: reverse
      tailed primer

<400> SEQUENCE: 31
accatgctcg agattacgag aaatgccaat ccctgtccta a                       41

<210> SEQ ID NO 32
<211> LENGTH: 41
<212> TYPE: DNA
<213> ORGANISM: Artificial Sequence
<220> FEATURE:
<223> OTHER INFORMATION: Description of artificial sequence: reverse
      tailed primer

<400> SEQUENCE: 32
gatcctaggc ctcacgtatt aaatgccaat ccctgtccta a                       41

<210> SEQ ID NO 33
<211> LENGTH: 38
```

```
<212> TYPE: DNA
<213> ORGANISM: Artificial Sequence
<220> FEATURE:
<223> OTHER INFORMATION: Description of artificial sequence: reverse
      tailed primer

<400> SEQUENCE: 33
accatgctcg agattacgag ggaaatgcca atccctgt                              38

<210> SEQ ID NO 34
<211> LENGTH: 38
<212> TYPE: DNA
<213> ORGANISM: Artificial Sequence
<220> FEATURE:
<223> OTHER INFORMATION: Description of artificial sequence: reverse
      tailed primer

<400> SEQUENCE: 34
gatcctaggc ctcacgtatt ggaaatgcca atccctgt                             38

<210> SEQ ID NO 35
<211> LENGTH: 39
<212> TYPE: DNA
<213> ORGANISM: Artificial Sequence
<220> FEATURE:
<223> OTHER INFORMATION: Description of artificial sequence: reverse
      tailed primer

<400> SEQUENCE: 35
accatgctcg agattacgag taagggggaa atgccaatc                            39

<210> SEQ ID NO 36
<211> LENGTH: 39
<212> TYPE: DNA
<213> ORGANISM: Artificial Sequence
<220> FEATURE:
<223> OTHER INFORMATION: Description of artificial sequence: reverse
      tailed primer

<400> SEQUENCE: 36
gatcctaggc ctcacgtatt taagggggaa atgccaatc                            39

<210> SEQ ID NO 37
<211> LENGTH: 62
<212> TYPE: DNA
<213> ORGANISM: Homo sapiens
<220> FEATURE:
<221> NAME/KEY: misc_feature
<222> LOCATION: (34)..(34)
<223> OTHER INFORMATION: n= c or t
<220> FEATURE:
<221> NAME/KEY: misc_feature
<222> LOCATION: (46)..(46)
<223> OTHER INFORMATION: n= a, c, g, or t

<400> SEQUENCE: 37
ttaagtatta catgtaaatt aatctaaact tttnttgaat ccagtngtgt tttcagcaag     60
ta                                                                   62

<210> SEQ ID NO 38
<211> LENGTH: 33
<212> TYPE: DNA
<213> ORGANISM: Artificial Sequence
<220> FEATURE:
<223> OTHER INFORMATION: Description of artificial sequence: primer

<400> SEQUENCE: 38
ttaagtatta catgtaaatt aatctaaact ttt                                  33
```

```
<210> SEQ ID NO 39
<211> LENGTH: 41
<212> TYPE: DNA
<213> ORGANISM: Artificial Sequence
<220> FEATURE:
<223> OTHER INFORMATION: Description of artificial sequence: primer

<400> SEQUENCE: 39
ggggcccctt aagtattaca tgtaaattaa tctaaacttt t                              41

<210> SEQ ID NO 40
<211> LENGTH: 37
<212> TYPE: DNA
<213> ORGANISM: Artificial Sequence
<220> FEATURE:
<223> OTHER INFORMATION: Description of artificial sequence: primer

<400> SEQUENCE: 40
agtattacat gtaaattaat ctaaacttt catgaat                                   37

<210> SEQ ID NO 41
<211> LENGTH: 37
<212> TYPE: DNA
<213> ORGANISM: Artificial Sequence
<220> FEATURE:
<223> OTHER INFORMATION: Description of artificial sequence: primer

<400> SEQUENCE: 41
agtattacat gtaaattaat ctaaacttt tatgaat                                   37

<210> SEQ ID NO 42
<211> LENGTH: 47
<212> TYPE: DNA
<213> ORGANISM: Artificial Sequence
<220> FEATURE:
<223> OTHER INFORMATION: Description of artificial sequence: primer

<400> SEQUENCE: 42
accatggtca cgattacgag tacttgctgc aaacacgact ggattca                       47

<210> SEQ ID NO 43
<211> LENGTH: 47
<212> TYPE: DNA
<213> ORGANISM: Artificial Sequence
<220> FEATURE:
<223> OTHER INFORMATION: Description of artificial sequence: primer

<400> SEQUENCE: 43
gatcctaggc ctcactgtta tacttgctgc aaacacgact ggattca                       47
```

METHODS FOR DETECTING POLYMORPHISMS IN NUCLEIC ACIDS

1. FIELD OF THE INVENTION

The present invention relates to the fields of molecular biology, chemistry, nucleic acid hybridization and genotyping. In certain embodiments, the present invention provides methods and compositions that are useful for scoring polymorphisms in nucleic acids.

2. BACKGROUND OF THE INVENTION

Most genetic differences between individuals are single-nucleotide polymorphisms (SNPs). At most SNP positions, there are two possible alleles. Such SNPs are distributed throughout the genome at frequency of about 1 per 1,000 base pairs. Several hundred thousand SNP markers are now available in public databases. These databases should facilitate the identification of genetic markers associated with disease. SNP scoring assays can determine which allele an individual has for an SNP of interest. A series of suitably designed SNP scoring assays can be used to link an SNP with a disease. However, in order to associate thousands of SNP markers with individual diseases, millions of SNP scoring assays must be carried out in large populations. Therefore, efficient methods to rapidly score SNPs at low cost for large populations are needed to utilize genetic markers for the mapping of disease genes and the effective diagnosis, treatment or prevention of the disease.

Several methods based on the migration of Holliday junctions in nucleic acids are capable of detecting SNPs under certain conditions (see, e.g., U.S. Pat. No. 6,013,439, U.S. Pat. No. 6,232,104 B1 and PCT publication WO 01/69200). In general, these methods can be used to detect differences between the sequences of two nucleic acids. For example, these methods can be used to detect sequence differences between a first nucleic acid with a known sequence and a second nucleic acid with an unknown sequence. For these methods to be used accurately, the two nucleic acids should have the same sequences everywhere except at the site of the polymorphism. If the nucleic acids have the same genotype, Holliday junction migration can proceed through the lengths of the nucleic acids. If the sequences of the nucleic acids differ, Holliday junction migration can halt at a site of sequence difference under the appropriate conditions. Detection of stabilized Holliday junctions can indicate that the sequence of the second nucleic acid differs from that of the first nucleic acid.

Although current Holliday junction detection methods can be used to detect differences between the sequences of two nucleic acids, they cannot be applied to compare the genotypes of all nucleic acids accurately. Current Holliday junction methods require that the nucleic acids have a minimum of about 100 base pairs, especially for the detection of single base mismatches. Most single mismatches between two nucleic acids shorter than 100 base pairs in length do not create sufficient energy barriers to impede branch migration for detection of stable Holliday junctions. Thus, most single base mismatches, for example at the site of an SNP, are capable of detectably impeding Holliday junction migration only if the nucleic acids are at least about 100 base pairs in length. Current methods are therefore often limited to the determination of the genotypes of nucleic acids at least about 100 base pairs in length.

Yet even when applied to nucleic acids greater than 100 base pairs in length, current methods can suffer from inaccuracies. Frequently, more than one SNP can be found within nucleic acid, e.g., a sample of genomic DNA, that is 100 base pairs in length. The frequency only increases as the length of the nucleic acid increases. If a pair of nucleic acids has more than one SNP in their lengths, current Holliday junction methods can only indicate that the nucleic acids differ in genotype somewhere in their sequences. They cannot resolve the difference or differences to particular SNPs.

There is a need for improved Holliday junction methods of scoring SNPs that can be used to accurately identify the genotype of an individual SNP in a given nucleic acid. The methods should be capable of application to nucleic acids of any length, including those of less than 100 base pairs. They should also be capable of resolving the genotypes of individual SNPs, even in nucleic acids comprising multiple SNPs.

3. SUMMARY OF THE INVENTION

The present invention provides improved methods of scoring SNPs by detecting the branch migration, e.g., Holliday junction migration, in a complex of two nucleic acids. Significantly, the methods can be applied to nucleic acids of any length, including nucleic acids much shorter than 100 base pairs in length. In addition, the methods can be used to resolve the genotype of an individual SNP in a nucleic acid comprising multiple SNPs.

In one aspect, the present invention provides methods for comparing the genotypes of two nucleic acids, e.g., a reference nucleic acid and a target nucleic acid. In the methods, constructs called partial duplexes, described below, can be prepared from and/or corresponding to the reference nucleic acid and target nucleic acid. The partial duplexes generally comprise sequences from the reference nucleic acid and target nucleic acid that include a polymorphism of interest. Advantageously, to avoid interference from other polymorphisms that might be present in the nucleic acids, the target and reference polynucleotide sequences can be short enough so that the probability of a second polymorphism other than the polymorphism of interest is minimized. The sequences can even be much less than 100 base pairs in length.

In order to compare accurately the genotypes of nucleic acids less than 100 base pairs in length, one or more mismatches can be introduced into the partial duplexes near the site of the polymorphism of interest. Although most single-base mismatches do not create energy barriers strong enough to impede branch migration between two duplexes if the duplexes are shorter than 100 bp long, double or multiple-base mismatches create greater energy barriers and are capable of impeding branch migration between two shorter duplexes. In certain embodiments, further modifications of the partial duplexes can be made to increase the sensitivity of the methods. For example, the melting temperature of the partial duplexes can be increased with methods known to those of skill in the art for increasing the stability of a duplex, such as the use of GC clamps, the use of peptide nucleic acids (PNAs) or the use of minor groove binding motifs.

Typically, the target nucleic acid is double stranded or single stranded and comprises a target polynucleotide sequence including the site of a polymorphism. To determine the genotype of the polymorphism, a target partial duplex is prepared comprising the target polynucleotide sequence or a mutated target polynucleotide sequence. A target partial duplex is a double stranded nucleic acid sequence wherein a section of one of the strands is complementary to the other strand and can anneal to form a partial duplex, but the full lengths of the strands are not complementary, resulting in at least one single-stranded polynucleotide tail at one or both ends of the partial duplex. The complementary portion of the target partial duplex should comprise the polymorphism of interest. A target partial duplex can be prepared, for example, by PCR using tailed-primers followed by denaturation/re-annealing (see, e.g., U.S. Pat. No. 6,013,439, U.S. Pat. No. 6,232,104 B1 and PCT publication WO 01/69200, the contents of which are hereby incorporated by reference in their entireties). In addition, a target partial duplex can be prepared by hybridization of an appropriate synthetic single stranded oligonucleotide to a single stranded oligonucleotide derived from the target nucleic acid.

A reference polynucleotide sequence corresponds to the target polynucleotide sequence and also comprises the site of the polymorphism. Typically, the genotype of the polymorphism of the reference polynucleotide sequence is known. To determine the genotype of the polymorphism, a reference partial duplex is prepared comprising the reference polynucleotide sequence including the site of the polymorphism or a mutated reference polynucleotide sequence. A reference partial duplex is a double stranded nucleic acid sequence wherein a section of one of the strands is complementary to the other strand and can anneal to form a partial duplex, but the full lengths of the strands are not complementary, resulting in a single-stranded polynucleotide tail at at least one end of the partial duplex. The complementary portion of the reference partial duplex should comprise the site of the polymorphism. A reference partial duplex can be prepared, for example, by hybridization of two single-stranded oligonucleotides that are partially complementary or by PCR using tailed-primers followed by denaturation/re-annealing (see, e.g., U.S. Pat. No. 6,013,439, U.S. Pat. No. 6,232,104 B1 and PCT publication WO 01/69200).

In certain embodiments of the invention, the reference partial duplex comprises a mutated reference polynucleotide sequence. A mutated reference polynucleotide sequence comprises a version of the reference polynucleotide sequence having a mutation near the site of the polymorphism. The mutation can be introduced, for example, in the primers used to prepare the reference partial duplex by PCR. Alternatively, the mutation can be introduced in the two oligonucleotides that hybridize to form a reference partial duplex. The mutation can be a single base change and can be, for example, less than 20 nucleotides of the site of the polymorphism. Preferably, the mutation is a nucleotide adjacent to the site of the polymorphism.

In other embodiments of the invention, the target partial duplex comprises a mutated target polynucleotide sequence. A mutated target polynucleotide sequence comprises a version of the target polynucleotide sequence having a mutation near the site of the polymorphism. The mutation can be introduced, for example, in the primers used to prepare the partial target duplex from the target nucleic acid by PCR. The mutation can be a single base change and can be, for example, less than 20 nucleotides away from the site of the polymorphism. Preferably, the mutation is at a nucleotide adjacent to the site of the polymorphism.

In further embodiments of the invention, both the target partial duplex and the reference partial duplex can comprise a mutated target polynucleotide sequence and a mutated reference polynucleotide sequence, respectively. The mutations can be prepared as described in the preceding paragraphs. Preferably, at least one of the mutations in the reference partial duplex is not identical to any of the mutations in the target partial duplex.

In the methods, the target partial duplex and reference partial duplex are contacted under conditions in which they are capable of forming a four-way complex. A four-way complex is a macromolecular structure that comprises both nucleic acids in double stranded form. Typically, a four-way complex comprises a Holliday junction. A Holliday junction is known to those of skill in the art as the branch point in a complex of two related (often identical) double stranded nucleic acids. If the nucleic acids share identical sequences and the sequence identity extends to the ends of the nucleic acids, the four-way complex is capable of undergoing branch migration under the appropriate conditions resulting in resolution into two double stranded sequences. Significantly, if sequence identity and complementarity does not extend to the ends of the nucleic acids, migration of the four-way complex can encounter an energy barrier at or near a site where the sequences are not identical or complementary. If the energy barrier is sufficient, the barrier can impede migration of the four-way complex at or near the site where the sequences are not identical or complementary.

The conditions under which the nucleic acids are contacted are chosen so that the four-way complex is capable of branch migration. Such conditions are known to those of skill in the art and include those under which migration of a four-way junction can proceed along the strands of the nucleic acids that comprise identical or complementary sequences. Typically, conditions are chosen such that allele-specific four-way complex migration is achieved. Under conditions appropriate for allele-specific four-way complex migration, four-way complex migration will proceed to completion thereby resolving two double stranded polynucleotides from the complex if the target partial duplex and the reference partial duplex share sequence identity at the site of polymorphism of interest. However, if the target partial duplex comprises and the reference partial duplex do not share sequence identity at the site of polymorphism of interest, four-way complex migration will not go to completion and the strands of the complex will not be resolved. A stable or immobilized four-way complex can form.

Detection of the stable four-way complex can indicate that the genotype of the reference polynucleotide sequence is not identical to the genotype of the target polynucleotide sequence at the site of polymorphism of interest. Stable or immobilized four-way complexes can be detected according to methods described herein. Moreover, detection of resolved four-way complexes can indicate that the genotype of the reference polynucleotide sequence is identical to the genotype of the target polynucleotide sequence at the site of polymorphism of interest. Resolved nucleic acids can be detected according to methods described herein.

The methods and compositions of the invention can be used in any application for which the genotyping of a nucleic acid is useful. Such applications include genotyping, SNP identification, SNP scoring, nucleic acid sequencing, and so forth. The methods and compositions of the invention provide sensitive and efficient methods of genotyping any polymorphism in a nucleic acid including a single nucleotide polymorphism.

4. BRIEF DESCRIPTION OF THE FIGURES

Figure 1B:
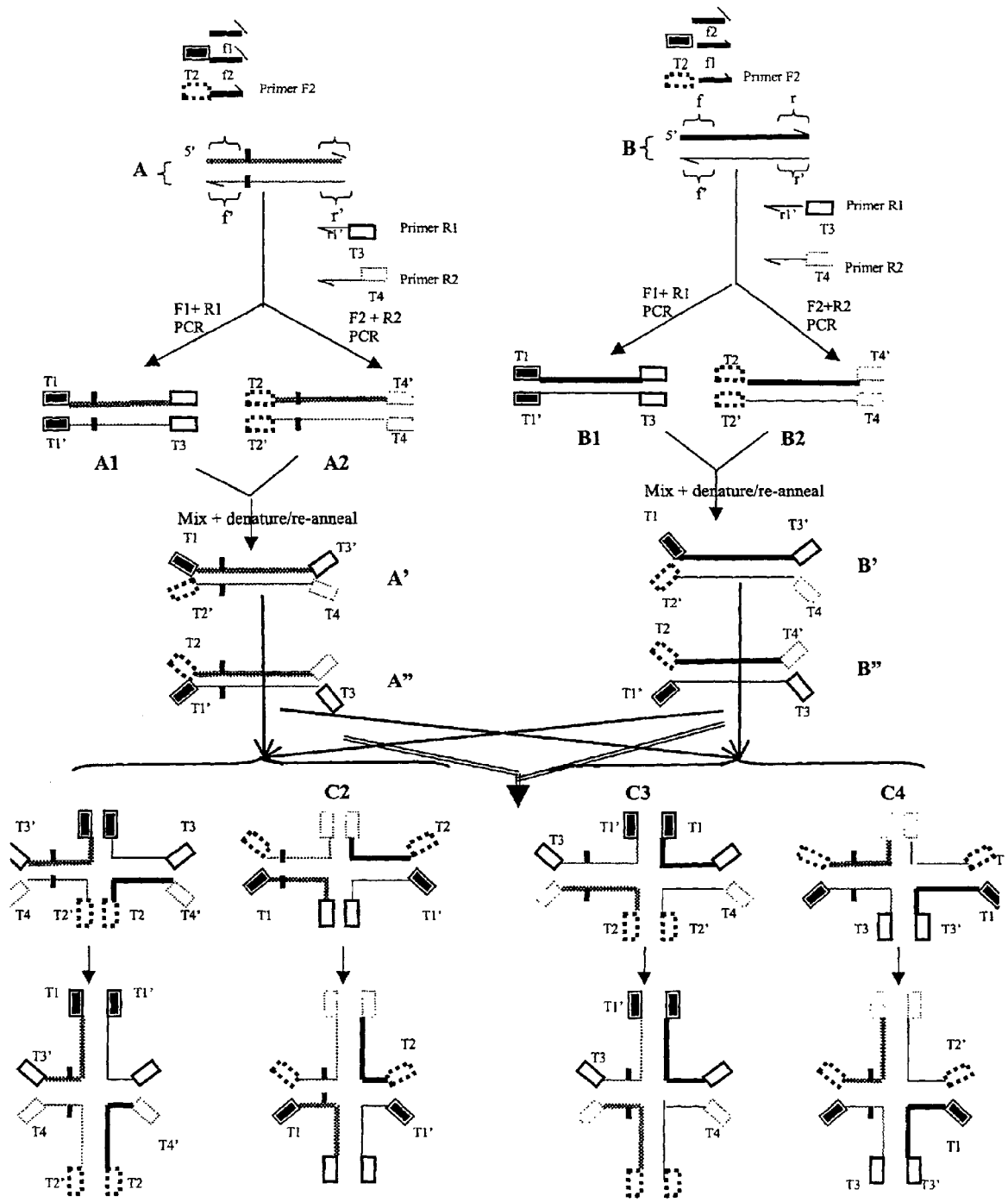
Figure 2:
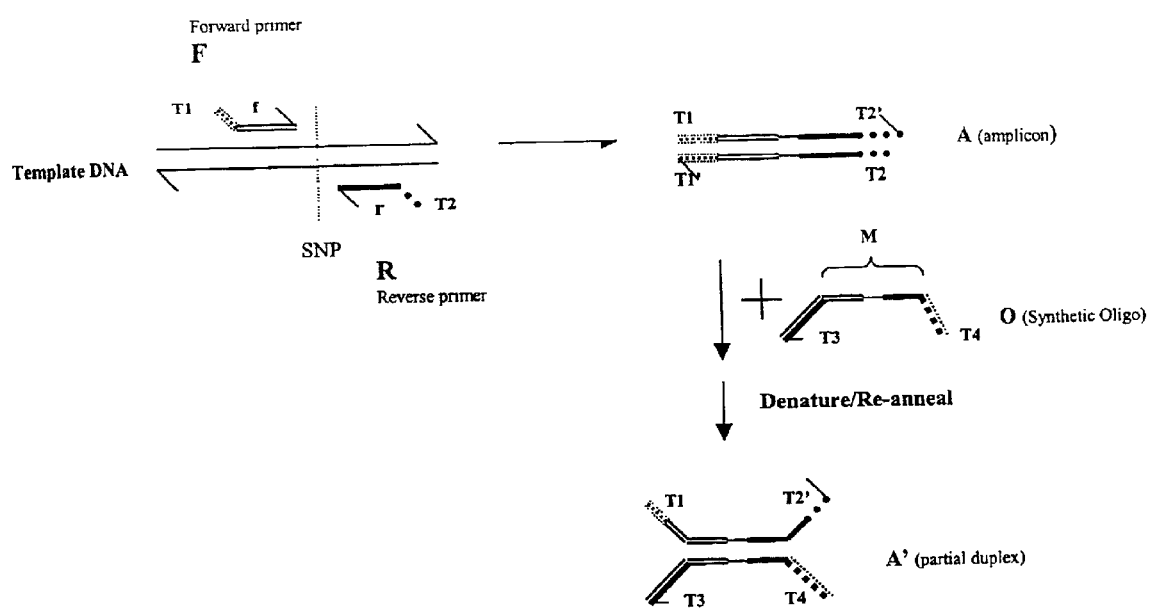
Figure 3:
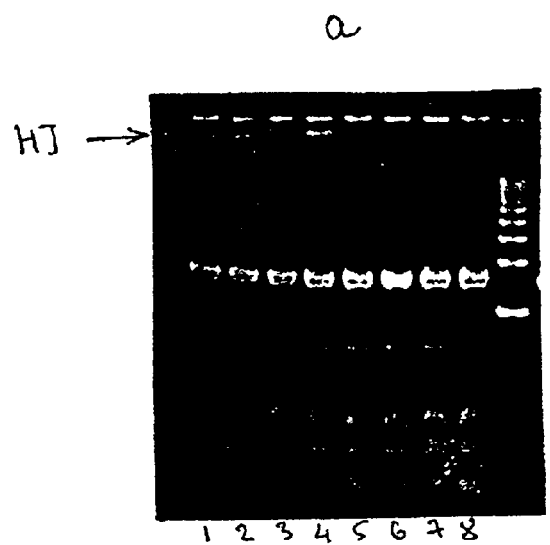
Figure 3:
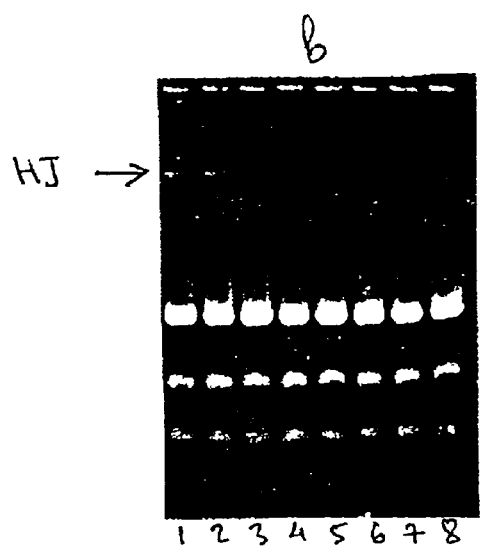

FIG. 1A and FIG. 1B provides an illustration of the preparation of a typical partial duplex of nucleic acids by PCR and formation of four-way complexes C1, C2, C3, and C4, which are then subject to branch migration conditions; FIG. 1A illustrates that if there is no mismatch between sequences A and B, each of the four complexes C1, C2, C3, and C4 resolves into duplexes; and FIG. 1B illustrates that if there is a mismatch or mismatches between sequences A and B, each of the four complexes C1, C2, C3, and C4 forms a stabilized four-way complex;

FIG. 2 provides an illustration of the preparation a typical partial duplex of nucleic acids by hybridization of a PCR product and a synthetic partially complementary oligonucleotide;

FIG. 3a and FIG. 3b provide photographs of a gel electrophoresis analysis of genomic DNA assayed for the genotype of a polymorphism according to conventional techniques. FIG. 3a presents eight samples amplified with PCR primers F-1(T1-1+T2-1) in lanes 1–8, respectively. FIG. 3b Presents eight samples amplified with PCR primers F-2(T1-1+T2-2) in lanes 1–8, respectively.

FIG. 4a and FIG. 4b provide photographs of a gel electrophoresis experiment illustrating that impeding branch migration of a four-way complex depends on the nature of mismatches. FIG. 4a presents eight samples with the a indicated mismatches amplified with PCR primers F-1(T1-1+T2-1) in lanes 1–8, FIG. 4b presents eight samples with the a indicated mismatches amplified with PCR primers F-2(T1-1+T2-2) in lanes 1–8.

Figure 5:
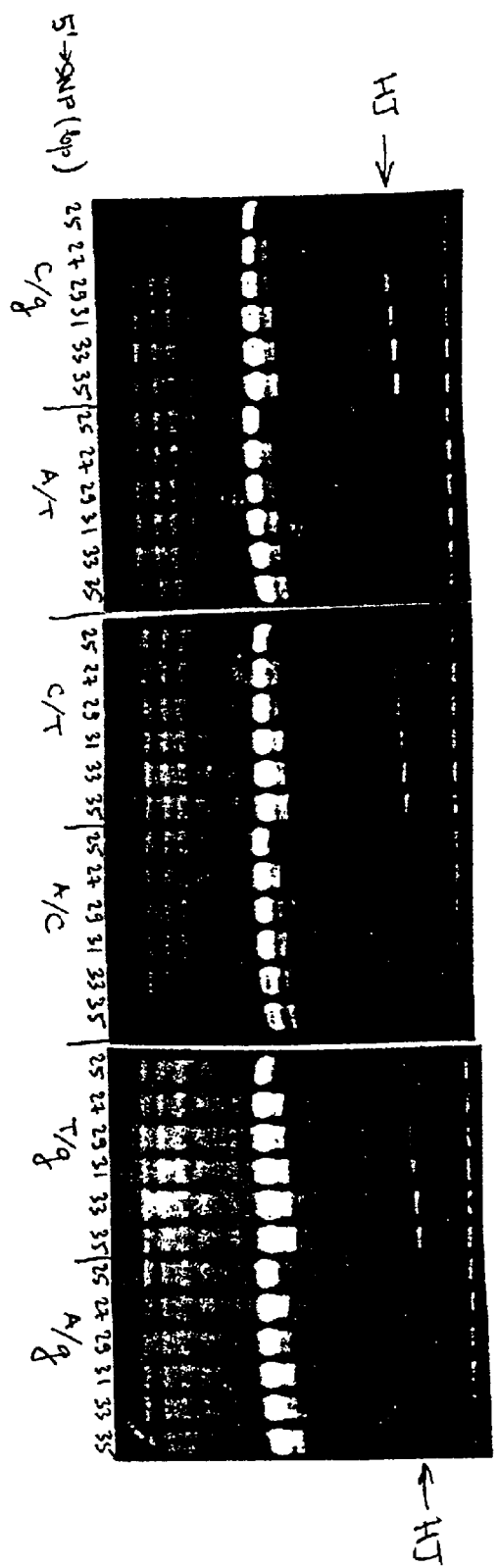
Figure 6A:
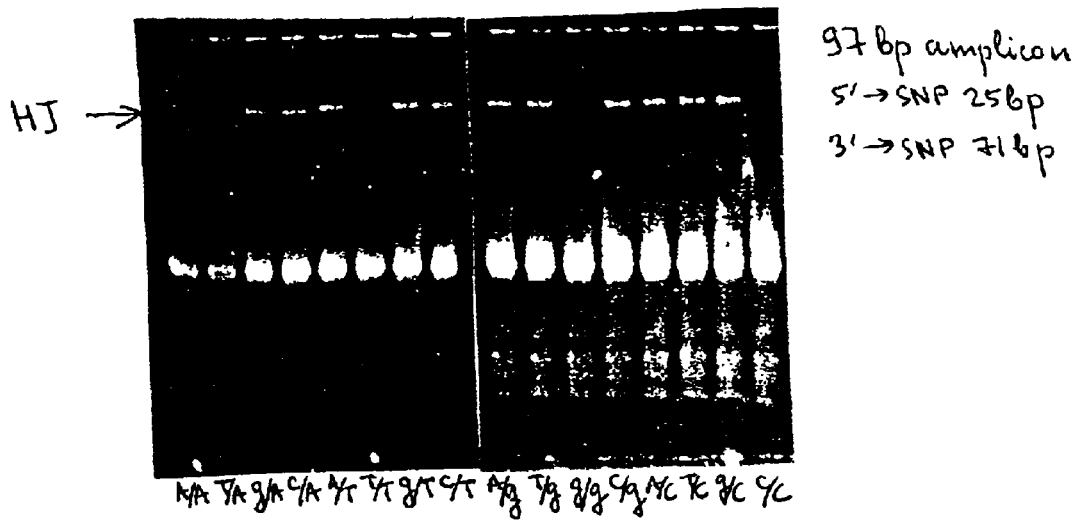
Figure 6A:
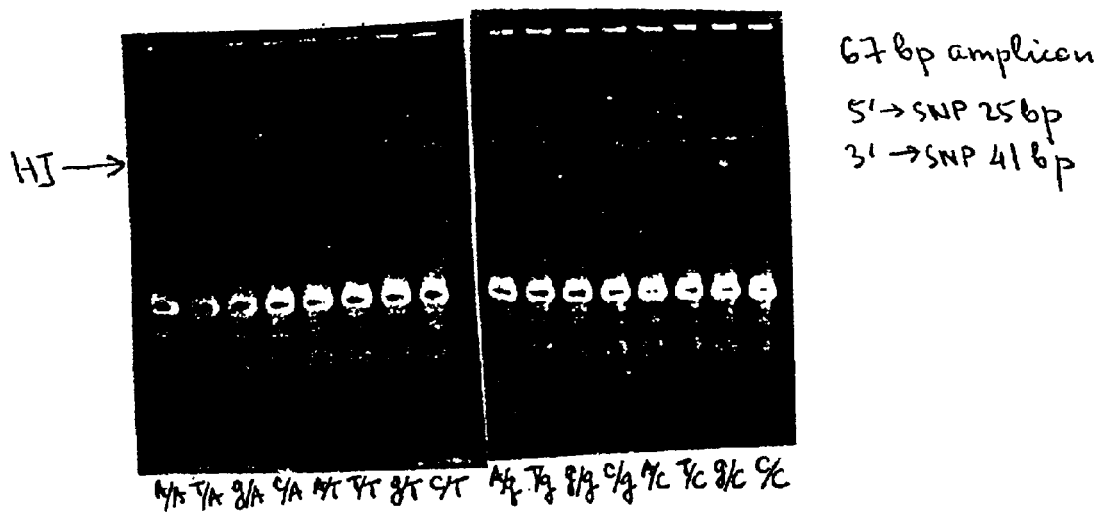
Figure 6B:
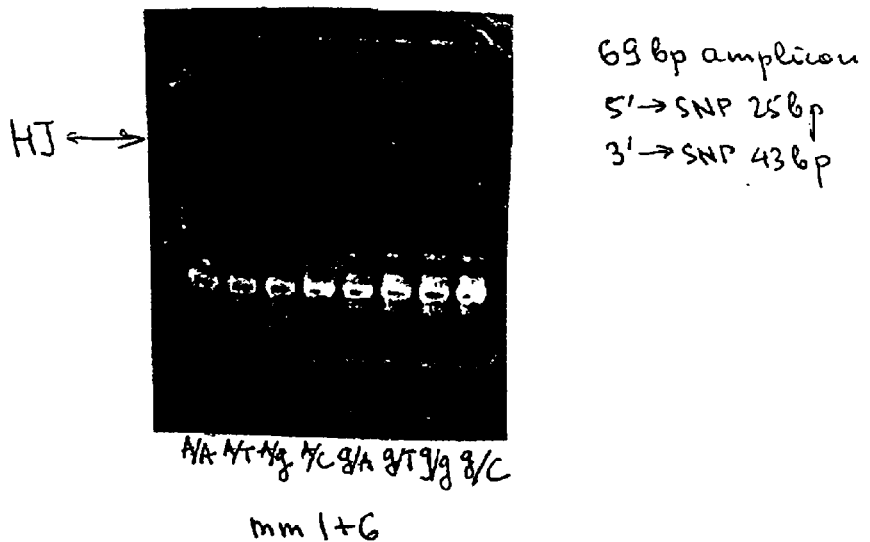
Figure 6B:
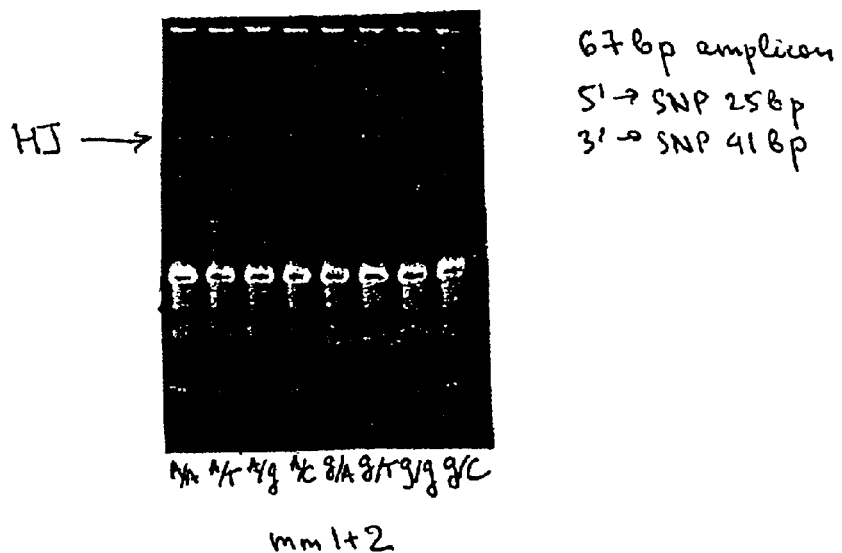
Figure 6C:
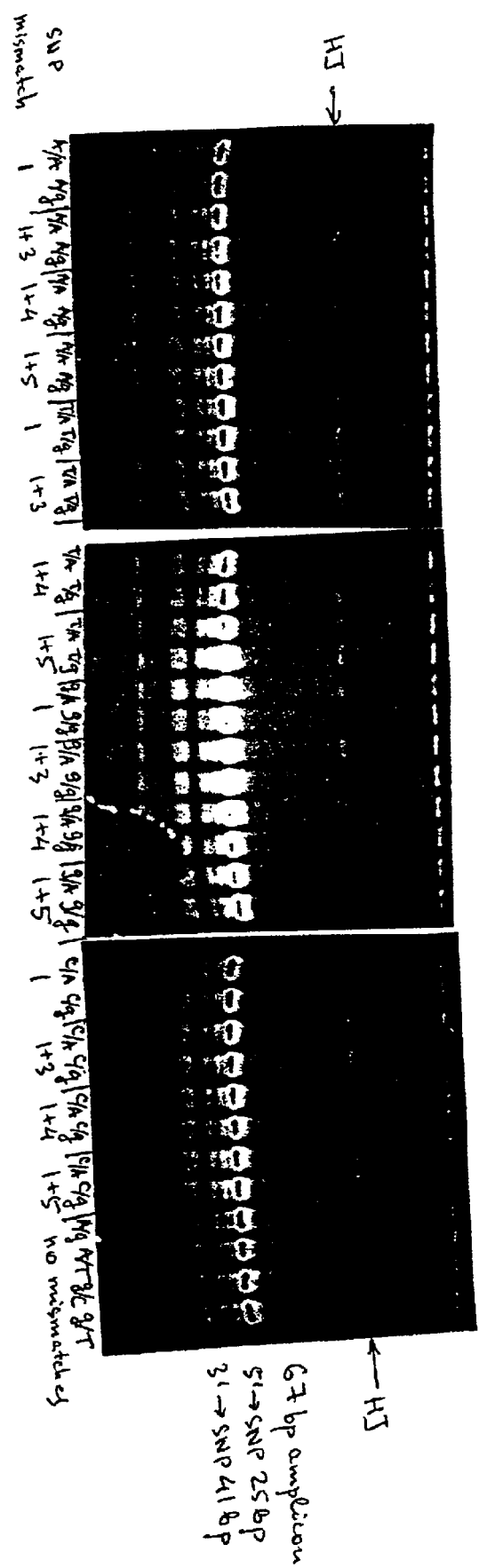
Figure 7:
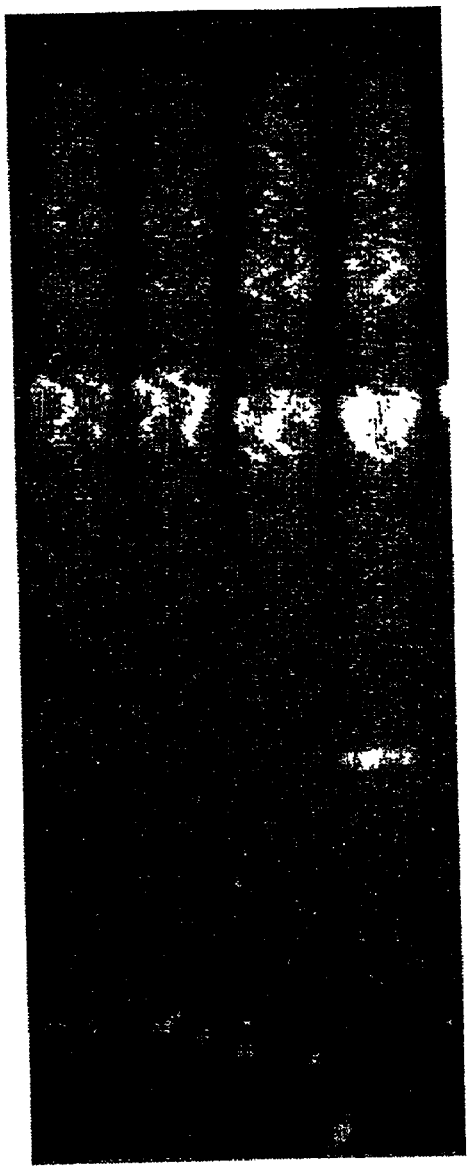

FIG. 5 provides a photograph of a gel electrophoresis experiment illustrating that impeding branch migration also depends on the size of an amplicon;

FIG. 6A, FIG. 6B and FIG. 6C provide photographs of a gel electrophoresis experiment illustrating the multiple mismatches improve impeding of branch migration and allow scoring of individual SNPs even in small amplicons. FIG. 6A shows that introduction of one extra A-T mismatch just 5' of the SNP (mm1) results in elimination of the differences in inhibitory effects of various mismatches at the SNP position for both 97 and 67 bp amplicons. FIG. 6B shows that second mismatches just 3' of the SNP (mm1+6) and 4 nucleotides from the first mismatch (mm1+2) proved to be too much in that resulted in the appearance of HJ band in A/A and G/G homozygotes. FIG. 6C shows that three remaining combinations (mm1+3, 1+4 and 1+5) appeared to be acceptable judging by the gel picture;

FIG. 7 provides a photograph of a gel electrophoresis experiment illustrating that a GC clamp improves the accuracy of the genotyping method.

5. DETAILED DESCRIPTION OF THE PREFERRED EMBODIMENTS 5.1 Abbreviations

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Also, unless specified otherwise, nucleic acid sequences that are represented as a series of one-letter abbreviations are presented in the 5'->3' direction.

5.2 Definitions

As used herein, the terms "nucleic acid" and "polynucleotide" are interchangeable and refer to any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

The terms nucleic acid, polynucleotide, and nucleotide also specifically include nucleic acids composed of bases other than the five biologically occurring bases (adenine, guanine, thymine, cytosine and uracil). For example, a polynucleotide of the invention might contain at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6- isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acidmethylester, 3-(3-amino-3-N-2-carboxypropyl) uracil, (acp3)w, and 2,6- diaminopurine.

Furthermore, a polynucleotide of the invention may comprise at least one modified sugar moiety selected from the group including but not limited to arabinose, 2-fluoroarabinose, xylulose, and hexose. It is not intended that the present invention be limited by the source of the polynucleotide. The polynucleotide can be from a human or non-human mammal, or any other organism, or derived from any recombinant source, synthesized in vitro or by chemical synthesis. The polynucleotide may be DNA, RNA, cDNA, DNA-RNA, peptide nucleic acid (PNA), a hybrid or any mixture of the same, and may exist in a double-stranded, single-stranded or partially double-stranded form. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, and the like.

The nucleic acid can be only a minor fraction of a complex mixture such as a biological sample. The nucleic acid can be obtained from a biological sample by procedures well known in the art.

A polynucleotide of the present invention can be derivitized or modified, for example, for the purpose of detection, by biotinylation, amine modifictaion, alkylation, or other like modification. In some circumstances, for example where increased nuclease stability is desired, the invention can employ nucleic acids having modified internucleoside linkages. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylenesulfide, dimethylenesulfoxide, dimethylene-sulfone, 2'-O-alkyl, and 2'-deoxy-2'-fluoro phosphorothioate internucleoside linkages are well known in the art (see, Uhlman et al., 1990, *Chem. Rev.* 90:543–584; Schneider et al. 1990, *Tetrahedron Lett.* 31:335, and references cited therein).

The term "oligonucleotide" refers to a relatively short, single stranded polynucleotide, usually of synthetic origin. An oligonucleotide typically comprises a sequence that is 8 to 100 nucleotides, preferably, 20 to 80 nucleotides, and more preferably, 30 to 60 nucleotides in length. Various techniques can be employed for preparing an oligonucleotide utilized in the present invention. Such an oligonucleotide can be obtained by biological synthesis or by chemical synthesis. For short sequences (up to about 100 nucleotides) chemical synthesis will frequently be more economical compared to biological synthesis. In addition to economy, chemical synthesis provides a convenient way of incorporating low molecular weight compounds and/or modified bases during synthesis. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing, 1983, *Methods Enzymol.* 101:20–78. Other methods of oligonucleotide synthesis include phosphotriester and phosphodiester methods (Narang et al., 1979, *Meth. Enzymol.* 68:90) and synthesis on a support (Beaucage et al., 1981, *Tetrahedron Letters* 22:1859–1862) as well as phosphoramidate synthesis, Caruthers et al., 1988, *Meth. Enzymol.* 154:287–314, and others described in "Synthesis and Applications of DNA and RNA," S. A. Narang, editor, Academic Press, New York, 1987, and the references contained therein.

An oligonucleotide "primer" can be employed in a chain extension reaction with a polynucleotide template such as in, for example, the amplification of a nucleic acid. The oligonucleotide primer is usually a synthetic oligonucleotide that is single stranded, containing a hybridizable sequence at or near its 3'-end that is capable of hybridizing with a defined sequence of the target or reference polynucleotide. Normally, the hybridizable sequence of the oligonucleotide primer has at least 90%, preferably 95%, most preferably 100%, complementarity to a defined sequence or primer binding site. In certain embodiments of the invention, the sequence of a primer can vary from ideal complementarity to introduce mutations into resulting amplicons, as discussed below. The number of nucleotides in the hybridizable sequence of an oligonucleotide primer should be such that stringency conditions used to hybridize the oligonucleotide primer will prevent excessive random non-specific hybridization. Usually, the number of nucleotides in the hybridizable sequence of the oligonucleotide primer will be at least ten nucleotides, preferably at least 15 nucleotides and, preferably 20 to 50, nucleotides. In addition, the primer may have a sequence at its 5'-end that does not hybridize to the target or reference polynucleotides that can have 1 to 60 nucleotides, 5 to 30 nucleotides or, preferably, 8 to 30 nucleotides.

The term "sample" refers to a material suspected of containing a nucleic acid of interest. Such samples include biological fluids such as blood, serum, plasma, sputum, lymphatic fluid, semen, vaginal mucus, feces, urine, spinal fluid, and the like; biological tissue such as hair and skin; and so forth. Other samples include cell cultures and the like, plants, food, forensic samples such as paper, fabrics and scrapings, water, sewage, medicinals, etc. When necessary, the sample may be pretreated with reagents to liquefy the sample and/or release the nucleic acids from binding substances. Such pretreatments are well known in the art.

The term "amplification," as applied to nucleic acids refers to any method that results in the formation of one or more copies of a nucleic acid, where preferably the amplification is exponential. One such method for enzymatic amplification of specific sequences of DNA is known as the polymerase chain reaction (PCR), as described by Saiki et al., 1986, *Science* 230:1350–1354. Primers used in PCR can vary in length from about 10 to 50 or more nucleotides, and are typically selected to be at least about 15 nucleotides to ensure sufficient specificity. The double stranded fragment that is produced is called an "amplicon" and may vary in length form as few as about 30 nucleotides to 20,000 or more. The term "chain extension" refers to the extension of a 3'-end of a polynucleotide by the addition of nucleotides or bases. Chain extension relevant to the present invention is generally template dependent, that is, the appended nucleotides are determined by the sequence of a template nucleic acid to which the extending chain is hybridized. The chain extension product sequence that is produced is complementary to the template sequence. Usually, chain extension is enzyme catalyzed, preferably, in the present invention, by a thermostable DNA polymerase, such as the enzymes derived from *Thermis acquaticus* (the Taq polymerase), *Thermococcus litoralis*, and *Pyrococcus furiosis*.

A "Holliday junction" is the branch point in a four-way junction in a complex of two related (often identical) nucleic acid sequences and their complementary sequences. The junction is capable of undergoing branch migration resulting in dissociation into two double stranded sequences where sequence identity and complementarity extend to the ends of the strands. Holliday junctions, their formation and branch migration are concepts familiar to those of skill in the art, and are described, for example, by Whitby et al., 1996, *J. Mol. Biol.* 264:878–890, and Davies & West, 1998, *Current Biology* 8:727–727.

"Branch migration conditions" are conditions under which migration of a four-way complex can proceed along the component polynucleotide strands. Normally in the practice of the invention, conditions are chosen such that migration will proceed only if strand exchange does not result in an increase in the number of mismatches in the complementary regions of the four-way complex, wherein a net increase in the number of base mismatches can impede branch migration, resulting in a stabilized four-way complex. Appropriate conditions can be found, for example, in Panyutin and Hsieh, 1993, *J. Mol. Biol.* 230:413–424. In certain applications the conditions will have to be modified due to the nature of the particular polynucleotides involved. Such modifications are readily discernible by one of skill in the art without undue experimentation.

A "stabilized" four-way complex is a junction where a mismatch has stalled branch migration to an extent sufficient that the stabilized four-way complex is detectable and distinguishable from the duplex DNA that would be released from a four-way complex involving identical sequences owing to branch migration.

Two nucleic acid sequences are "related" or "correspond" when they are either (1) identical to each other, or (2) would be identical were it not for some difference in sequence that distinguishes the two nucleic acid sequences from each other. The difference can be a substitution, deletion or insertion of any single nucleotide or a series of nucleotides within a sequence. Such difference is referred to herein as the "difference between two related nucleic acid sequences."

Frequently, related nucleic acid sequences differ from each other by a single nucleotide. Related nucleic acid sequences typically contain at least 15 identical nucleotides at each end but have different lengths or have intervening sequences that differ by at least one nucleotide.

The term "mutation" refers to a change in the sequence of nucleotides of a normally conserved nucleic acid sequence resulting in the formation of a mutant as differentiated from the normal (unaltered) or wild type sequence. Mutations can generally be divided into two general classes, namely, base-pair substitutions and frame-shift mutations. The latter entail the insertion or deletion of one to several nucleotide pairs. A difference of one nucleotide can be significant as to phenotypic normality or abnormality as in the case of, for example, sickle cell anemia.

A "duplex" is a double stranded nucleic acid sequence comprising two complementary sequences annealed to one another. A "partial duplex" is a double stranded nucleic acid sequence wherein a section of one of the strands is complementary to the other strand and can anneal to form a partial duplex, but the full lengths of the strands are not complementary, resulting in a single-stranded polynucleotide tail at at least one end of the partial duplex.

The terms "hybridization," "binding" and "annealing," in the context of polynucleotide sequences, are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is typically achieved by elevating the temperature, increasing the ratio of cosolvents, lowering the salt concentration, and other such methods well known in the field.

Two sequences are "complementary" when the sequence of one can bind to the sequence of the other in an antiparallel sense wherein the 3'-end of each sequence binds to the 5'-end of the other sequence and each A, T(U), G, and C of one sequence is then aligned with a T(U), A, C, and G, respectively, of the other sequence.

A "detection molecule" is any molecule that is capable of selectively binding a four-way complex of nucleic acids such as a Holliday junction. Suitable detection molecules are known to those of skill in the art and include, but are not limited to RuvA, RuvC, RuvB, RusA, RuvG, and mutants, analogs or fragments thereof. "Mutants" of detection molecules include detection molecules comprising mutations that retain their capability of selectively binding a four-way complex of nucleic acids. Examples of such mutants are described below. "Analogs" of detection molecules include, for example, analogs of RuvA, RuvC, RuvB, RusA and RuvG isolated from species other than *E. coli*. Preferred analogs include thermostable analogs.

A "tracer molecule" is any molecule capable of selectively binding the detection molecule. When co-existing in solution, the tracer molecule can compete with the four-way complex for binding to the detection molecule. Preferably, the tracer molecule comprises one or more oligonucleotides that are capable of forming a stable or immobile four-way complex and a detectable label.

5.3 Methods of Genotyping a Target Nucleic Acid

The present invention is universal and permits scoring of the genotype of any polymorphism in any nucleic acid. The polymorphism can be any polymorphism in a nucleic acid sequence, e.g., a single or multiple base substitution or polymorphism, a deletion or an insertion. Methods of the invention are rapid, convenient, and amenable to automation, and can be conducted in a homogeneous or heterogeneous format. They are ideally suited for rapid mutation genotyping, particularly involving the genotyping of single nucleotide polymorphisms (SNPs). The disclosed methods are sensitive and quantitative and are particularly amenable to application with polymerase chain reaction (PCR).

The present invention is based, in part, on the surprising discovery that the introduction of extra mismatches into one or more nucleic acids can improve the sensitivity of genotyping methods based on the migration of four-way complexes of nucleic acids. In the conventional methods, two nucleic acids are contacted under conditions in which they are capable of forming a four-way complex and in which the four-way complex is capable of migration. If a difference between the nucleic acids at the site of the polymorphism creates a sufficient energy barrier to migration of the four way complex, the difference can impede migration, and the impeded four-way complex can be detected. However, as shown in the Examples below, mismatches in certain four-way complexes cannot be detected according to conventional methods, especially when such methods are applied to short nucleic acids.

The methods of the present invention, on the other hand, have sufficient accuracy to detect virtually any mismatch, even in complexes of short nucleic acids. While not to be bound by any particular theory of operation, the extra mismatches of the instant invention can create an energy barrier to migration of a four-way complex that increases the likelihood that a difference at a site of a polymorphism will impede migration of a four-way complex, particularly in short nucleic acids, e.g., those less than 100 base pairs in length.

In general, the present invention provides methods useful for the scoring of the genotype of a polymorphism of a target nucleic acid. In the methods, a target polynucleotide sequence of the target nucleic acid is compared with the sequence of a reference nucleic acid that comprises a known genotype of the polymorphism. In particular, the methods determine whether a construct comprising the target polynucleotide sequence (target partial duplex, discussed below) and a construct comprising a reference polynucleotide sequence of the reference nucleic acid (reference partial duplex, discussed below) are capable of forming a stabilized four-way complex. Significantly, a mutation is introduced into one of the constructs near the site of the polymorphism to achieve allele-specific four-way complex formation. In certain embodiments, further modification of the partial duplexes can be used to increase the accuracy of allele-specific four-way complex formation.

Detection of a stabilized four-way complex can indicate that the target nucleic acid and reference nucleic acid differ in genotype at site of polymorphism in question. Detection of resolution of the four-way complex can indicate that the target nucleic acid and reference nucleic acid share the same genotype. Specific embodiments of the invention are disclosed herein to illustrate the invention and to enable one skilled in the art to practice the invention. The specific embodiments are not intended to limit the scope of the invention.

5.3.1 The Target Nucleic Acid

As illustrated in FIG. 1, the invention provides methods and compositions for identifying the genotype of a target nucleic acid A at the site of a polymorphism of interest by means of allele-specific formation of a four-way complex of nucleic acids comprising the sequences. Typically, the target nucleic acid A comprises a target polynucleotide sequence whose genotype at the site of the polymorphism of interest is to be assayed. The target nucleic acid A can be obtained from any source according to methods know to those of skill in the art. For example, the target nucleic acid can be genomic DNA, or a fragment thereof, isolated from any of the samples described in detail above.

The target polynucleotide sequence can be of any length so long as the target partial duplex, together with the reference partial duplex (described below), is capable of allele-specific four-way complex migration. Significantly, the methods of the present invention allow allele-specific four-way complex migration even when the target polynucleotide sequence is less than 100 base pairs in length. In preferred embodiments of the invention, the target polynucleotide sequence is at least 8 base pairs, 10 base pairs, 20 base pairs, 30 base pairs, 40 base pairs in length. The target polynucleotide sequence can be as long as desired. Preferably, the target polynucleotide sequence is not so long that the target polynucleotide sequence comprises the sites of more than one polymorphism.

According to certain embodiments of the invention, a target partial duplex A' comprising the target polynucleotide sequence is prepared. In other embodiments of the invention, a target partial duplex A' comprising a mutated target polynucleotide sequence is prepared. Significantly, a mutated target polynucleotide sequence is a version of the target polynucleotide sequence wherein a mutation is introduced near the site of the polymorphism in question. The mutation can be any mutation in the target polynucleotide sequence. The introduced mutation can, for example, create an extra mismatch between the target polynucleotide sequence and the reference polynucleotide sequence. The extra mismatch by itself should not impede branch migration and cause the formation of stable Holliday Junctions. However the extra mismatch, when coupled with a mismatch at the site of the polymorphism of interest, should impede branch migration and cause the formation of stable Holliday Junctions.

Although the mutation can be any mutation in the target polynucleotide sequence, single nucleotide substitutions, single nucleotide deletions or single nucleotide insertions are preferred. Moreover, the mutation can be at any location within the target polynucleotide sequence. The nucleotide can be 3' or 5' to the site of the polymorphism. But preferably, the mutation is less than 20 nucleotides from the site of the polymorphism. More preferably, the mutation is introduced at the nucleotide next to the site of the polymorphism. The mutation can be either 3' or 5' of the site of the polymorphism. A mutated target polynucleotide sequence can also comprise additional mutations relative to the target polynucleotide sequence.

In certain embodiments, further modifications of the partial duplex, in addition to the introduced mutation described above, can be used to increase the accuracy of the methods. Typically, such modifications include those known to those of skill in the art to increase the melting temperature of a duplex. For instance, GC clamps can be added at either end of the target polynucleotide sequence by, for example, PCR techniques. In addition, minor groove binding motifs can be added to either strand of the partial duplex. Furthermore, the backbone of the partial duplex such as a DNA duplex can be modified to increase stability by, for example, substitution with an RNA backbone, a PNA backbone or another backbone known to those of skill in the art.

Partial duplexes and their preparation are described in detail in U.S. Pat. No. 6,013,439, in U.S. Pat. No. 6,232,104 B1 and in PCT publication WO 01/69200, each of which is hereby incorporated by reference in its entirety.

A typical partial duplex A' is illustrated in FIG. 1. Partial duplex A' comprises a complementary duplex region and one or more tail regions. A complementary duplex region comprises a target polynucleotide sequence or a reference polynucleotide sequence annealed to its complement. Other examples of partial duplexes are illustrated as A", B' and B".

In partial duplex A', one tail region comprises the oligonucleotide tails T1 and T2'. Similarly, a second tailed region comprises the oligonucleotide tails T3' and T4. Tail T1, T2, T3' and/or T4 can be linked to the target polynucleotide sequence via any linkage known to those of skill in the art for linking polynucleotides. They can be linked directly via a covalent bond or via a linker. The linker can be a polynucleotide or any other linker known to those of skill in the art. Preferably, tail T1 and/or T3' is linked to the target polynucleotide sequence directly via a phosphodiester linkage. In a similar fashion, tail T1, T2, T3, T4, T1', T2', T3' and/or T4' can be linked to a target polynucleotide sequence or a reference polynucleotide sequence.

In some embodiments of the invention, a partial duplex has one tail region. In other embodiments of the invention, a partial duplex has two tail regions. Tails T1, T2', T3' and T4 are preferably 5 bp-500 bp and more preferably 5 bp–55 bp.

All four tails are comprised of sequences that are unrelated to each other and to the template DNA, or alternatively, one of the pair of polynucleotide tails at each terminus of the partial duplexes (T1/T2' or T3'/T4) can be template DNA sequences. Preferably, a tail is capable of hybridizing with another sequence that complements the tail without interference from the target polynucleotide sequence, the reference polynucleotide sequence (described below) or from other tails. So that they are capable of forming a four-way structure, two or more partial duplexes can be prepared with the same target polynucleotide sequence and a corresponding reference polynucleotide sequence. For instance, partial duplexes A' and B", illustrated in FIG. 1, are capable of forming a four-way structure under the appropriate conditions. In FIG. 1, partial duplex A' comprises the tails T1, T2', T3', and T4. Another partial duplex B" comprises the tails T1', T2, T3 and T4'. Each pair of polynucleotide tails at each end of the partial duplexes, e.g., T1/T2', T2/T1', T3'/T4, T3/T4' are not complementary and will not anneal to one another under the applicable conditions. However, tail T3' at the right end of partial duplex A' is complementary to, and hence can hybridize with, tail T3 at the right end of partial duplex B". Tail T4 at the right end of partial duplex A' is complementary to, and hence can hybridize with, tail T4' at the right end of partial duplex B". Tail T1 at the left end of partial duplex A' is complementary to, and hence can hybridize with, tail T1" at the left end of partial duplex B". Tail T2' at the left end of partial duplex A' is complementary to, and hence can hybridize with, tail T2 at the left end of partial duplex B".

5.3.2 The Reference Nucleic Acid

In order to determine the genotype of the target nucleic acid, the target nucleic acid can be compared to a reference nucleic acid. The reference nucleic acid can be any nucleic acid that comprises a reference polynucleotide sequence containing the polymorphism. Preferably, the genotype of the reference nucleic acid at the site of the polymorphism of interest is known. Typically, the reference polynucleotide sequence is a sequence of the reference nucleic acid that is related to the target polynucleotide sequence of the target nucleic acid B. The sequences can be related if the they are either identical, or would be identical if not for some difference between the two sequences, for example, at the site of the polymorphism.

The reference polynucleotide sequence can be of any length so long as the reference partial duplex, together with the target partial duplex, is capable of allele-specific four-way complex migration. Significantly, the methods of the present invention allow allele-specific four-way complex migration even when the reference polynucleotide sequence is less than 100 base pairs in length. In preferred embodiments of the invention, the reference polynucleotide sequence is at least 8 base pairs, 10 base pairs, 20 base pairs, 30 base pairs, 40 base pairs in length. The reference polynucleotide sequence can be as long as desired. Preferably, the reference polynucleotide sequence is not so long that the reference polynucleotide sequence comprises the sites of more than one polymorphism.

Preparation of a reference partial duplex is illustrated in FIG. 1. According to certain embodiments of the invention, a reference partial duplex B' is prepared comprising the reference polynucleotide sequence. In other embodiments of the invention, reference partial duplex B' is prepared comprising a mutated reference polynucleotide sequence, discussed below.

The reference partial duplex B' comprises a complementary region and one or more tail regions T1/T2' and/or T3'/T4. The complementary region should comprise a substantial portion of the reference polynucleotide sequence or mutated reference polynucleotide sequence. In the complementary region of the reference partial duplex, the two strands of the nucleic acid are capable of hybridizing under the appropriate conditions. In preferred embodiments, the two strands in the complementary region are perfectly complementary. A tail region T1/T2' or T3'/T4 of the reference partial duplex can be at either end of the reference partial duplex, or tail regions T1/T2' and T3'/T4 can be at both ends of the reference partial duplex. In the tail region T1/T2' or T3'/T4, the two strands of the reference partial duplex should not be capable of hybridizing under the appropriate conditions. Preferably, the two strands of the reference partial duplex share no significant complementarity in the tail region. Significantly, the sequence of each strand of the tail region T1/T2' or T3'/T4 should be chosen so that the reference partial duplex B' is capable of forming a four-way complex with the target partial duplex A". Reference partial duplexes that are capable of forming a four way complex with target partial duplexes are described extensively in U.S. Pat. No. 6,013,439, in U.S. Pat. No. 6,232,104 B1 and in PCT publication WO 01/69200.

Significantly, in certain embodiments of the invention, the reference partial duplex comprises a mutated reference polynucleotide sequence. A mutated reference polynucleotide sequence is a version of the reference polynucleotide sequence wherein a mutation is introduced near the site of the polymorphism to improve the sensitivity of the method. The introduced mutation can, for example, create an extra mismatch between the reference polynucleotide sequence and the target polynucleotide sequence. The extra mismatch by itself should not impede branch migration and cause the formation of stable Holliday Junctions so that branch migration can proceed when there is no mismatch at the site of the polymorphism of interest. However the extra mismatch, when coupled with a mismatch at the site of the polymorphism of interest, should impede branch migration and cause the formation of stable Holliday Junctions. Exemplary extra mismatches are discussed in the Examples below.

The mutation can be any mutation in the reference polynucleotide sequence, and single nucleotide substitutions are preferred. The mutation can be at any location within the reference polynucleotide sequence. Preferably, the mutation is less than 20 nucleotides from the site of the polymorphism. Most preferably, the mutation is adjacent to the site of the polymorphism. The mutation can be 3' or 5' to the site of the polymorphism. A mutated reference polynucleotide sequence can comprise additional mutations relative to the reference polynucleotide sequence.

According to the methods of the invention, the partial duplexes should have a mismatch that is not at site of the polymorphism. Thus, if the target partial duplex comprises no mutation near the site of the polymorphism, then the reference partial duplex should preferably comprise a mutation near the site of the polymorphism. On the other hand, if the reference partial duplex comprises no mutation near the site of the polymorphism, then the target partial duplex should preferably comprise a mutation near the site of the polymorphism.

In embodiments where the reference partial duplex and the target partial duplex both comprise mutations, at least one of the mutations in the reference partial duplex should preferably not be identical to any of the mutations in the target partial duplex. As discussed above, the extra mutations by themselves should not impede branch migration and cause the formation of stable Holliday Junctions. However the extra mutations, when coupled with a mismatch at the site of the polymorphism of interest, should impede branch migration and cause the formation of stable Holliday Junctions.

5.3.3 Preparation of Nucleic Acids

The partial duplexes described above can be prepared by any method known to those of skill in the art for the preparation of polynucleotides or nucleic acids. For instance, the partial duplexes can be prepared by standard recombinant, synthetic or PCR techniques, or a combination thereof. In addition, the partial duplexes, or portions thereof such as the target or reference polynucleotide sequence, can be isolated from natural sources. Exemplary methods of preparing sequences that are capable of forming partial duplexes are described in U.S. Pat. No. 6,013,439, in U.S. Pat. No. 6,232,104 B1 and in PCT publication WO 01/69200, each of which is hereby incorporated by reference in its entirety. Furthermore, partial duplexes can be prepared by hybridization with one or more synthetic polynucleotides.

For example, partial duplexes can be prepared by the following PCR techniques. FIG. 1 illustrates the preparation of partial duplexes A', A", B' and B" by a PCR technique. To prepare the partial duplexes, nucleic acids A and B can be amplified, either separately or jointly, by standard PCR using a common set of primers made up of one or more forward primers and two reverse primers R1 & R2. R1 and R2 can either share the same 3' end (r'=r1'=r2') that hybridizes to the same part of template DNA or the 3' end of R1 and R2 can hybridize to different parts of the template DNA (r1'≠r2'). As illustrated in FIG. 1, forward primer F1 or forward primer F2 can be used in the PCR reaction. If forward primer F1 is used, duplexes with T1/T1' tails will be generated such as A1. If forward primer F2 is used, duplexes with T2/T2' tails will be generated such as A2. Two forward primers can also be used to generate partial duplexes at the end corresponding to the forward primer. For instance, using forward primers F1 and F2 in the same PCR reaction generates sequences that can be used to produce partial duplexes A' and A". In addition, a forward primer with no tails can be used to generate a duplex with no tails at the end corresponding to the forward primer.

The entire sequence of the forward primer F hybridizes with the template DNA, i.e., both A and B. Forward primers F1 and F2 can share their 3' end (f1=f2) and hybridize with the same part of template DNA (reference and target DNA), or alternatively, primer F1 and F2 can have different 3' ends and therefore hybridize with different parts of template DNA (f1≠f2). In addition, F1 has a 5'-end portion (T1) that does or does not hybridize with the template DNA. Likewise, F2 has a 5'-end portion (T2) that does or does not hybridize with the template DNA. The two reverse primers R1 and R2 can share a common 3'-end portion (r'=r1'=r2') that hybridizes with the same part of template DNA, or alternatively, primer R1 and R2 can have different 3' end and therefore hybridize with different part of template DNA. In addition, R1 has a 5'-end portion (T3) that does not hybridize with the template DNA. Likewise, R2 has a 5'-end portion (T4) that is not complementary to and hence does not hybridize with the template DNA. T3 is not related with T4, i.e., the complementary strand of T3 (T3') is not complementary to T4 and the complementary strand of T4 (T4') is not complementary to T3. As a result, T4' will not hybridize with T3 under the conditions employed in the method. Multiple rounds of PCR amplification will result in the formation of a number of DNA products, including the component strands of the four tailed partial duplexes A', A", B', B" (FIG. 1). The tailed duplexes are formed by adjusting the temperature of the solution so that the component strands can hybridize to form the desired partial duplexes. Note that a number of other duplexes will also be formed. These unintended products generally do not pose a problem because a sufficient number of partial duplexes are formed under the conditions described above.

Each tailed partial duplex A' is comprised of a duplex of two complementary nucleic acid strands of duplex A and, at one end of the duplex, two non-complementary oligonucleotide tails T3' and T4. Depending on the choice of forward primer, partial duplex A' can have either zero, one or two tails at the other end of the partial duplex (if T1=0 & T2=0, then a partial duplex can be produced with no tails at left end; if T1=0 or T2=0, then a partial duplex can be produce with one tail at the left end; if T1≠T2≠0, then a partial duplex can be produced with two non-complementary tails at the left end). Each tailed partial duplex A" is comprised of a duplex of two complementary nucleic acid strands of duplex A and, at one end of the duplex, two non-complementary oligonucleotide tails T4' and T3. Depending on the choice of forward primer, partial duplex A" can have either zero, one or two tails at the other end of the partial duplex (see, supra). Each tailed partial duplex B' is comprised of a duplex of two complementary nucleic acid strands of duplex B and, at one end of the duplex, two non-complementary oligonucleotide tails T3' and T4, Depending on the choice of forward primer, partial duplex B' can have either zero/one/two tails at the other end of the partial duplex (see, supra). Each tailed partial duplex B" is comprised of a duplex of two complementary nucleic acid strands of duplex B and, at one end of the duplex, two non-complementary oligonucleotides T4' and T3. Depending on the choice of forward primer, partial duplex B" can have either zero, one or two tails at the other end of the partial duplex (see, supra).

In certain embodiments, target or reference partial duplexes can be prepared by hybridization of one strand of a PCR amplicon with a synthetic oligonucleotide that is partially complementary to the PCR amplicon. FIG. 2 illustrates the preparation of a partial duplex A' using this method. Amplicon A can be prepared by PCR using forward primer F and reverse primer R. The polymorphism of interest (SNP) should be located between F and R so that it is amplified from the template DNA. Primer F or R or both can be completely complementary to the template DNA (T1=0 or T2=0 or T1 & T2=0). Alternatively, primers F and R can have, in addition to 3' portions (f and r, respectively) that are complementary to the template DNA, 5' portions (T1 and T2, respectively) that are not complementary to the template DNA. While T1 and T2 are not complementary to each other, T1 can be complementary to T1' and T2 can be complementary to T2'.

Amplicon A can then be contacted with synthetic oligonucleotide O that is partially complementary to one strand of amplicon A. O can be composed of a middle part M, and a left portion T3 or a right portion T4, or both T3 and T4. M can be fully or partially complementary to a portion of amplicon A so that O and A can hybridize to form partial duplex A'. After denaturing/re-annealing, a partial duplex A' can form through hybridization of O and the portion of amplicon A that is fully or partially complementary to O. The site of the polymorphism of interest should be within a sequence that corresponds to M. At least one end of O (T3 or T4, or both T3 and T4) should not be complementary to amplicon A. When only one end (T3 or T4) is not complementary to amplicon A, one tailed region can form at one end of the partial duplex. When both ends (T3 & T4) are not complementary to amplicon A, two tailed region can form, one at each end. Although it is shown in FIG. 2 that part of f and r are included in M, it is possible that M does not contain any sequence of f or r. Alternatively, the whole sequence of f and/or r, their complements, or portions thereof can be included in M.

In certain embodiments of the invention, a reference partial duplex can be formed by the hybridization of two synthetic oligonucleotides that correspond to the target sequence. The reference partial duplex is described in detail above. One or both strands of the reference partial duplex can be prepared by synthetic methods known to those of skill in the art. The strands of the reference partial duplex can then be contacted with each other under conditions wherein they are capable of hybridizing to form a reference partial duplex.

If a partial duplex is to comprise a mutation near the site of the polymorphism, the mutation can be introduced into the partial duplex according to any method known to those of skill in the art. For instance, the mutation can be introduced during preparation of the partial duplex by the use of a PCR primer comprising the mutation as is well known to those of skill in the art. In addition, in certain embodiments, a strand of the partial duplex can be synthesized comprising the appropriate mutation. Other methods of introducing a mutation near a site of a polymorphism in a partial duplex will be apparent to those of skill in the art.

This example and other methods of preparing partial duplexes should be apparent to the skilled artisan and fall within the scope of the instant invention.

5.3.4 Formation of a Four-Way Structure

In order to detect whether sequences A and B share the same genotype at the site of polymorphism in question, partial duplexes (A', A", B', B") comprising sequences A and B are brought into contact under conditions where the complementary tails are capable of annealing to one another, thereby initiating the formation of a four-way complex, as depicted in FIG. 1. Typical four-way complexes include Holliday junctions as are known to those of skill in the art. The resulting complexes C1, C2, C3, C4 are subjected to conditions where branch migration can occur. Branch migration is restricted from proceeding in the direction of the tails, because the tails on a given partial duplex are not complementary to one another, e.g., T1is not complementary to T2'. However, branch migration can occur in the other direction to the extent that the reference and target polynucleotide sequences do not have sufficient sequence differences to impede branch migration. Branch migration can proceed to the ends of the strands, resulting in the dissociation of the complex into two duplexes, each comprising one strand from each of the original partial duplexes (FIG. 1A). On the other hand, if the target and reference polynucleotide sequences have different genotypes at the site of the polymorphism of interest, branch migration past this point of difference will result in a mismatch in the newly formed duplex. Under the conditions used in the practice of the instant invention, the presence of such a difference will impede branch migration, resulting in a stabilized four-way complex (FIG. 1B). As a result, a difference in genotypes between the two sequences is manifested in the creation of a stabilized four-way complex that, in the absence of the difference, would resolve into two duplexes.

It will be apparent to the skilled artisan that the right terminus of the tailed partial duplex A' has, as the end part of each strand, sequence T4 and T3', respectively, that are complementary to T4' and T3, respectively, that are tails at the right terminus of B" and are not complementary to each other. When four-tailed partial duplexes A', A", B', B" are present in the same solution under the appropriate conditions, two four-way complexes (complex C1 and C2) comprising partial duplex A' and B" can form. One can form as the result of the hybridization of tail T1of A' with tail T1' of B" and hybridization of tail T2' of A' with tail T2 of B". Another can form as a result of the hybridization of tail T3' of A' with tail T3 of B" and the hybridization of tail T4 of A' with tail T4' of B". In addition, two more four-way complexes C3 and C4 can form partial duplexes A" and B'. One can form when tail T1' of A" hybridizes with tail T1of B' and when tail T2 of A" hybridizes with tail T2' of B'. The other can form when tail T3 of A' hybridizes with tail T3' of B' and when tail T4" of A" hybridizes with T4 of B'.

In addition, four tailed partial duplexes A', A", B' and B" can form concatemers. For instance, three partial duplexes B", A' and a second partial duplex B" can form a concatemer with two four-way complexes. However, concatemers do not prevent the detection of differences between sequence A and sequence B. If sequences A and B are identical, then migration of both four-way complexes in the B" -A' -B" should go to completion resulting in resolution of the entire concatemer into two duplexes. If there is a difference in genotype between sequences A and B, then both four-way complexes will be stabilized. Detection of the stabilized four-way complexes can indicate the difference between sequences A and B.

The skilled artisan using the teaching provided herein and knowledge generally available to the skilled artisan can determine appropriate conditions for hybridization of the tails and the resulting formation of a four-way complex of any specific duplexes. See, for example, Sambrook et al., *Molecular Cloning, A Laboratory Manual*, second edition, Cold Spring Harbor Laboratory (1989), Panyutin et al., supra, and U.S. Pat. No. 6,013,439. The four-way complexes C1, C2, C3 and C4 are subject to branch migration conditions wherein, because tails T1 and T2 and tails T3 and T4 are different, the branch migration can only proceed away from the tails whose hybridization initiates four-way complex formation. If there is no difference in genotype between A and B, the branch migration of complex C1, C2, C3 and C4 can proceed away from the tail all the way to the other end of the partial duplexes. As a result, each of the four complexes C1, C2, C3 and C4 resolve into duplexes (FIG. 1A). Alternatively, if there is a difference in genotype between A and B the branch migration of complex C1, C2, C3 and C4 proceeding in the direction away from the tail can be impeded by the mismatch(es) and stabilized four-way complexes C1, C2, C3 and C4 can form (FIG. 1B). In one embodiment of the invention, branch migration is conducted in the presence of an ion such as $Mg^{++}$, which enhances the tendency of a mismatch to impede spontaneous DNA migration and hence stabilizes four-way complexes involving such a mismatch. A preferred concentration range for $Mg^{++}$ is 1 to 10 mM. It should be noted that stabilization can be achieved by means of other ions, particularly divalent cations such $Mn^{++}$ or $Ca^{++}$, or by a suitable combination of ions. In a particularly preferred embodiment, branch migration is achieved by incubation at 65° C. for about 20–120 minutes in buffer containing 4 mM $MgCl_2$, 50 mM KCl, 10 mM Tris-HCl, pH 8.3. A description of branch migration conditions suitable for the formation of stabilized four-way complex as a consequence of a single base mismatch can be found, for example, in Panyutin and Hsieh, 1993, *J. Mol. Biol.* 230:413–424, which is hereby incorporated by reference in its entirety.

5.3.5 Detection of Four-Way Complexes

Detection of stable four-way complexes (C1, C2, C3 or C4) can be used as to indicate the presence of a difference between nucleic acids A and B and thereby a difference in the genotype of the target nucleic acid and the reference nucleic acid. The absence of stabilized four-way complexes, on the other hand, can be used to indicate the lack of a difference between nucleic acids A and B and thereby an identity of the genotype of the target nucleic acid and reference nucleic acid.

According to the present invention, the stabilized four-way complex indicative of a difference between nucleic acids A and B can be detected by any method known to those of skill in the art for detecting a four-way complex including, but not limited to, the methods described below.

For instance, a stabilized four-way complex can be detected by contacting the nucleic acids with an appropriate detection molecule, by electrophoresis or by any other technique described in U.S. Pat. No. 6,013,439, in U.S. Pat. No. 6,232,104 B1 and in PCT publication WO 01/69200. For example, a detection molecule can be used to detect a stabilized four-way complex. The detection molecule can be any molecule or molecules known to those of skill in the art to specifically bind four-way structures such as Holliday structures. In a preferred embodiment, a protein can be used to detect a stabilized four-way structure. Many proteins from various organisms have been shown specifically bind four-way structures. Those proteins include but are not limited to: RuvA, RuvC, RuvB, RusA, RuvG of *E. coli* and proteins/mutants derived from RuvA, RuvC, RuvB, RusA, RuvG. In addition, such proteins include homologs (such as functional homologs) of RuvA, RuvC, RuvB, RusA, RuvG from various other organisms, such as homologs of RuvA, RuvC, RuvB, RusA, and RuvG derived from mammals, Ccel and spCcel from yeast, Hjc from *Pyrococcus furiosusa*, and various other resolvases and recombinases that can specifically bind to four-way complexes.

In particularly convenient embodiments of the invention, thermostable proteins can be used to detect the presence of a four-way complex. Such thermostable proteins include thermostable homologs of RuvA, RuvC, RuvB, RusA, and RuvG that are derived from thermophilic organisms—organisms selected from the group consisting of *Thermus aquaticus, Thermus flavus, Thermus thermophilus* and other thermophilic organisms known to those of skill in the art. Hjc from *Pyrococcus furiosusa* is one example of an appropriate thermostable protein with specificity for four-way complexes.

The preparation and properties of a number of such proteins useful in the practice of the present invention have been described, for example, in the following list of literature references, all of which are incorporated herein in their entirety: Davies and West, supra; Whitby et al., supra; Iwasaki et al, 1992, *Genes Dev.* 6:2214–2220; Parsons et al., 1992, *Proc. Natl. Acad. USA* 89:5452–5456; Traneva et al., 1992, *Mol. Gen. Genet.* 235:1–10; Rafferty et al, 1996, *Science* 274:415–421; Hargreaves et al., 1999, *Acta Crystallogr. D. Biol. Crystallogr.* 55(Pt 1):263–265; Hargreaves et al., 1998, *Nature Struct. Biol.* 5(6):441–446; Dunderdale et al., 1994, *J. Biol. Chem.* 267 (7):5187–5194; Ariyoshi et al., 1994, *Cell* 78(6):1063–1072; Sharples et al., 1994, *EMBO* 13(24):6133–6142; Rice et al., 1995, *Cell* 82(2):209–220; Bujacz et al., 1995, *J. Mol. Biol* 253(2):333–346; Rice et al., 1996, *Curr. Opin. Struct. Biol.* 6(1):76–83; Suck, 1997, *Biopolymer* 44(4):405–421; White et al., 1997, *J. Mol. Biol.* 266(1):122–134; Whitby et al., 1997, *J. Mol. Biol.* 271(4):509–522; Bidnenko et al., 1998, *Mol. Microbiol.* 28(4): 823–834; Raaijmakers et al., 1999, *EMBO* 18(6):1447–1458; Komori et al., 1999, *Proc. Natl. Acad. Sci. USA* 96(16):8873–8; Komori et al., 2000, *J. Biol. Chem.* 275: 40385–40391; Sharples et al., 1999, *J. Bacteriol.* 181(8):554355–50; Sharples et al., 1993, *Nucleic Acid Research* 21(15):3359–64.

In certain preferred embodiments, the detection molecule is RuvA. The RuvA molecule can be wild-type RuvA or other useful RuvA molecules known to those of skill in the art. In other embodiments, the detection molecule can be a wild-type RuvC. Conveniently, the detection molecule can also be a RuvC mutant that lacks the wild-type enzyme's Holliday junction-specific endonuclease activity but retains the ability to specifically bind four-way complexes. Such mutants include D7N, E66Q, D138N, D141N, D7N, E66D, D138E, and ruvC51, and others described, for example, in Saito et al., 1995, *Proc Natl Acad Sci USA* 92:7470–7474 and in Sharples et al., 1993, *Nucleic Acid Research* 21:3359–3364, the contents of which are hereby incorporated by reference in their entireties.

In preferred embodiments of the invention, a stabilized four-way complex can be detected with a combination of a labeled tracer molecule and a detection molecule as described in U.S. application Ser. No. 10/071,299 which is hereby incorporated by reference in its entirety. Briefly, a tracer molecule comprises a stable or immobile four-way complex. Stable or immobile four-way complexes of oligonucleotides include those described in Shida et al., 1996, *J. Biochem.* 119:653–658 and in Pikkemaat et al., 1994, *Biochemistry* 33:14896–14907, the contents of which are hereby incorporated by reference in their entireties. The tracer molecule also comprises a detectable label. The detectable label can be any label that is capable of generating a signal that can be detected by methods known to those of skill in the art. Preferably, the signal can be sensitive to the binding of the tracer molecule by the detection molecule. In particular, the signal from a tracer molecule bound by a detection molecule should be distinguishable from the signal from an unbound tracer molecule.

To detect a stabilized four-way complex with a tracer molecule (described in U.S. application Ser. No. 10/071,299, the detection molecule can be contacted with the nucleic acids in a solution comprising a tracer molecule. The detection molecule can be contacted with the nucleic acids under conditions in which the detection molecule is capable of selectively binding the tracer molecule or a four-way complex. If the nucleic acids are capable of forming a stabilized four-way complex, the stabilized four-way complex can compete with the tracer molecule for binding by the detection molecule thereby altering the signal from the tracer molecule. The change in signal of the tracer molecule can indicate the presence of a stabilized four-way complex. Other methods of detecting stabilized four-way complexes will be apparent to those of skill in the art and can be used in the methods of the present invention.

Identification of a stabilized four-way complex can indicate that the target polynucleotide sequence and the reference polynucleotide sequence differ, thereby indicating that the target nucleic acid has a genotype that is different from the genotype of the reference nucleic acid. The absence of a stabilized four-way complex can indicate that the target polynucleotide sequence and the reference polynucleotide sequence are identical at the site of the polymorphism, thereby indicating that the genotype of the target nucleic acid is identical to the genotype of the reference nucleic acid. The invention having been described, the following examples are intended to illustrate, and not limit, this invention.

6. EXAMPLES

6.1 Example 1

Accurate Genotyping Requires Using PCR Primers that are Close to an SNP in Question Eight genomic DNA samples comprising the M08PDR panel (Coriell Cell Repository, Camden, N.J.) were amplified using the F-1/(T1-1+T2-1) and F-2/(T1-2+T2-2) primers (see, Table 3, infra) that generate 170 bp amplicons and 67 bp amplicons, respectively. PCR amplifications were carried out using a PTC-200 DNA Engine thermocycler (MJ Research Inc., Waltham, Mass.). 45 PCR cycles were performed with 10 s denaturation at 94° C., 15 s reannealing at 62° C., and a 45 s extension at 72° C. The cycling was preceded by a 10-min incubation at 95° C. to activate AmpliTaq Gold™ DNA polymerase (Applied Biosystems, Foster City, Calif.) and followed by 2 min of denaturation at 95° C. and 30-min incubation at 65° C. (reannealing and branch migration). The reaction mixtures (100 μL) contained 10 ng genomic DNA, 2.5 U AmpliTaq Gold™ DNA polymerase, 200 mM each dNTP, 500 nM of the forward primer and 250 nM each of the reverse tailed primers in BMB buffer (10 mM Tris-HCl, pH 8.3, 50 mM KCl, 4 mM MgCl2, 200 mg/ml BSA).

The genotypes of the 8 samples were determined by digesting the 170 bp amplicons with Dde I, a restriction endonuclease that cuts when there is a C and not a G at the SNP position. Samples 1 and 2 proved to be G/C heterozygotes, the other 6 samples-C/C homozygotes.

The PCR amplicons (5 ml each) were subject to branch migration and then analyzed in a 6% PAGE gel in TBE (Invitrogen Corp., San Diego, Calif.). The gels were stained with SYBR Gold (Molecular Probes, Eugene, Org.), visualized using a Dark Reader transilluminator (Clare Chemical Research, Denver, Colo.) and photographed using Kodak 667 film.

FIG. 3a presents eight samples amplified with PCR primers F-1/(T1-1+T2-1) in lanes 1–8, respectively. FIG. 3b presents eight samples amplified with PCR primers F-2/(T 1-1+T2-2) in lanes 1–8, respectively.

The Holliday junction (HJ) bands are observed in the lanes that correspond to samples 1 and 2 (FIG. 3a). The gel picture, however, revealed a HJ band with a slightly lower mobility in sample 4.This result indicates that there is a second SNP present somewhere in the 170 bp amplicon. This second SNP would cause false positives if a number of unknown genomic DNA samples were screened for the 4129 SNP using conventional Holliday Junction-based genotyping assays.

No HJ band is observed in sample 4 when both PCR primers are immediately adjacent to the 4129 GIC SNP (FIG. 3b). Therefore, to ensure accurate genotyping, the primers must be very close, preferably adjacent, to the SNP in question.

6.2 Example 2

The Amount of HJ Formation in Short Amplicons is Mismatch Specific

To find out if all possible SNPs can be assayed in short amplicons, all possible heterozygotes were generated by using forward primers (SEQ ID NOS: 3–7) that contain different "wobbles" at the SNP position. The wobbles overwrite the naturally occurring C in the genomic target thus generating a series of amplicons containing all possible SNPs at the same distance from both amplicon ends and in the same sequence environment. This approach is preferable to comparing various SNPs to each other in unrelated amplicons.

The forward primers containing wobbles were used in combination with either (T1-1+T2-1) or (T1-2+T2-2) reverse tailed primers to generate a 97 bp amplicon (5'-to-SNP distance 25 bp, 3'-to-SNP distance 71 bp, including the tails) and a 67 bp amplicon (5'-to-SNP distance 25 bp, 3'-to-SNP distance 41 bp, including the tails), respectively. The extent to which various mismatches impede branch migration in these amplicons was judged by the intensity of respective HJ bands in 6% PAGE.

FIG. 4a presents eight samples with the indicated mismatches amplified with PCR primers F-1/(T1-1+T2-1). FIG. 4b presents eight samples with the indicated mismatches amplified with PCR primers F-2/(T1-1+T2-1).

Figure 4:
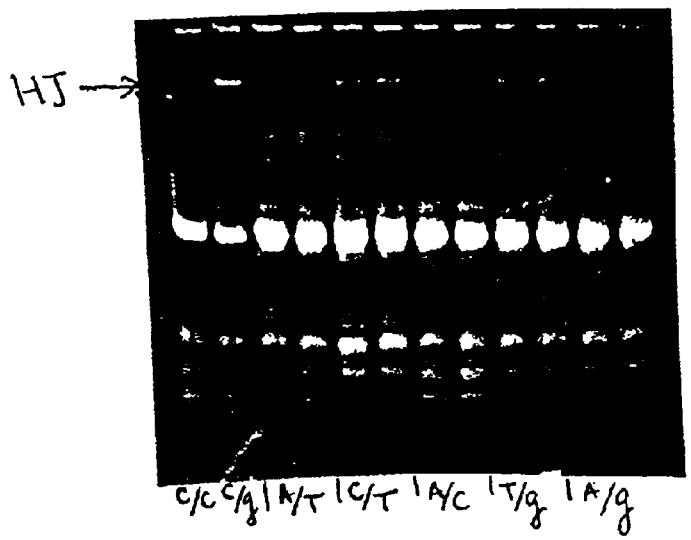
Figure 4:
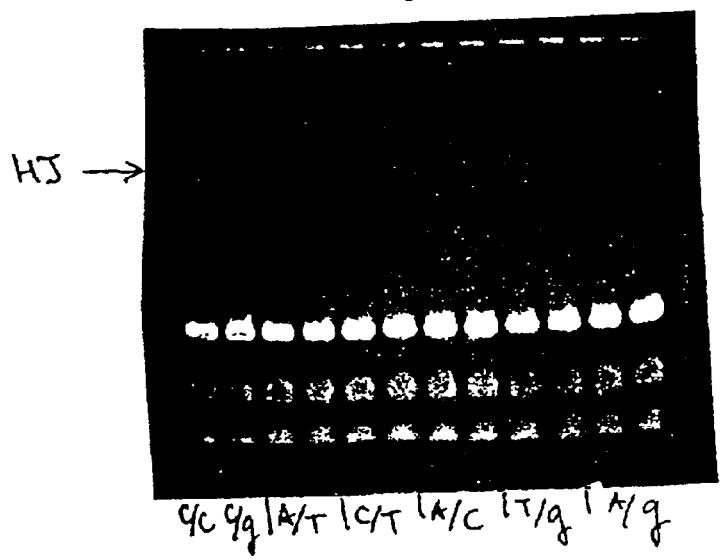

FIG. 4 shows that various mismatches indeed impede branch migration to a different extent. In the 97 bp amplicon (FIG. 4a), a single G→C mismatch produces the most intense HJ band, followed by a single T→G mismatch, a single C→T mismatch or a single A→C mismatch, whereas a single A→T mismatch or a single A→G mismatch practically does not produce any detectable HJ at all—judging by both the lack of HJ band on gel and the lack of inhibition in fluorescence polarization competition assays. The difference between various mismatches is even more dramatic in the 67 bp amplicon (FIG. 4b): the noticeable HJ band is produced only by a single G→C mismatch. The HJ band produced by a single T→G mismatch or a single C→T mismatch is barely visible.

6.3 Example 3

The Length of Amplicons Affects the Extent to Which Various Mismatches Impede Branch Migration One possible, though impractical, solution to the problem outlined in Example 2 is to increase the distance between the SNP and the 5'-end of the amplicon by using a longer forward primer. FIG. 5 illustrates this approach using the 97 bp amplicon above as an example. A series of progressively longer forward primers (SEQ ID NOS: 8–12) was designed by adding more nucleotides to the 5'-end of the F-2 primer in 2 nucleotides steps. The intensity of the HJ band increases with each such step for each of the mismatches. However, various mismatches continue to cause HJ formation to a different extent, G→C the most and A→C, A→G and A→T the least. Increasing the 3'-to-SNP distance is even less practical in view of the cost and deteriorating quality of the reverse tailed primers, which are more than 40 nucleotides in length. Reverse primers T-3 and T-4 (SEQ ID NOS: 33–36) whose 3'-ends are removed from the SNP by 5 and 10 nucleotides, respectively, were also examined. The conclusion was the same as for the forward primer: the longer the distance between the SNP/mismatch and the amplicon ends, the more HJ formation.

6.4 Example 4

Introduction of Additional Mismatches Greatly Increases HJ Formation in Short Amplicons A more ingenious approach to the short amplicon problem was the introduction of an extra "weak" mismatch (e.g., A→T, A→G, A→C) which by itself would be too weak to block branch migration in a homozygous short amplicon, but in combination with a natural mismatch in a heterozygote would be strong enough to block branch migration and cause HJ formation to a detectable level. Towards this end the forward primers (SEQ ID NOS: 17–28) were designed in which a T was substituted for a naturally occurring A (or vice versa) at different positions (the substituted bases are underlined). The cycle annealing temperature was reduced from 62° C. to 58° C. when amplifying a C/C homozygote in order to compensate for the multiple mismatches between the primers and target genomic DNA. These amplicons were mixed with equal aliquots of amplicons prepared from the same C/C homozygous genomic DNA using the forward primers without any additional mismatches (SEQ ID NOS: 13–16).

FIG. 6a shows that introduction of one extra A→T mismatch just 5' of the SNP (mm1) results in elimination of the differences in inhibitory effects of various mismatches at the SNP position for both 97 and 67 bp amplicons (Example 2, FIG. 4): the HJ bands in all the heterozygote lanes have the same intensity. There are no HJ bands in the homozygote (A/A, T/T, G/G and C/C) lanes. Results for the 97 bp amplicon are provided in the top photograph, and results for the 67 bp amplicon are provided in the bottom photograph.

The above results were also confirmed by performing fluorescence polarization (FP) competition assays on selected samples. 20 ml of PCR product was mixed with 80 ml 125 pM tracer (a synthetic immobile Holliday junction HJ18–2 with 18 nucleotide arms one of which is internally labeled with fluorescein, see, supra) and 1 ml 0.25 mM RuvA was added to this mixture. After 10 min. incubation at room temperature the fluorescence polarization of the samples was measured using the Beacon 2000 Fluorescence Polarization Analyzer (Pan Vera Corp., Madison, Wis.).

Table 1 confirms the conclusions drawn from the gel picture (FIG. 6). For the 97 bp amplicon the introduction of mismatch 1 simply eliminates the difference in causing HJ formation between the strong (G→C, G→T) and weak (A→G, A→C, A→T) mismatches at the SNP position, whereas for the 67 bp amplicon discrimination between the hetero- and homozygotes is possible only if the extra mismatch is present. However, in this experiment one additional mismatch is still not sufficient for detection of A/T heterozygote in the 67 bp amplicon.

TABLE 1

Fluorescence polarization (mp)

| SNP | 97 bp amplicon 5' > SNP 25 bp; 3' > SNP 71 bp | | 67 bp amplicon 5' > SNP 25 bp; 3' > SNP 41 bp | |
|---|---|---|---|---|
| | No mismatches | Mismatch 1 | No mismatches | Mismatch 1 |
| G/G | 193 | 168 | 224 | 169 |
| C/C | 193 | 138 | 182 | 187 |
| C/G | 88 | 96 | 153 | 129 |
| T/G | 97 | 85 | 172 | 120 |
| A/G | 145 | 89 | 205 | 135 |
| A/C | 156 | 97 | 181 | 139 |
| A/T | 155 | 84 | 250 | 174 |

Further improvements in the assay for the 67 bp amplicon were attempted by introducing a second additional mismatch at different positions. Second mismatches just 3' of the SNP (mm1+6) and 4 nucleotides from the first mismatch (mm1+2) proved to be too much in that they resulted in the appearance of HJ band in A/A and G/G homozygotes (FIG. 6b). Results for a 69 bp amplicon amplified with PCR primers F-2/(T1-3+T2-3) are provided in the top photograph, and results for the 67 bp amplicon are provided in the bottom photograph.

Three remaining combinations (mm1+3, 1+4 and 1+5) appeared to be acceptable judging by the gel picture (FIG. 6c): uniform HJ band intensity for various SNPs and its absence in the homozygotes. FIG. 6c provides results for the 67 bp amplicon. The first photograph provides results for two mismatches 8 bp 5' of the SNP position (mm1+3). The second photograph provides results for two mismatches 12 bp 5' of the SNP position (mm1+4). The third photograph provides results for two mismatches 16 bp 5' of the SNP position (mm1+5).

The results were again confirmed by FP competition assays for selected samples, which are summarized in Table 2.

TABLE 2

Fluorescence polarization (mp)

| SNP | No mismatches | mm1 | mm1 + 3 | mm1 + 4 | mm1 + 5 |
|---|---|---|---|---|---|
| G/G | 418 (1) | 446 (1) | 325 (1) | 263 (1) | 363 (1) |
| G/A | 353 (0.84) | 252 (0.57) | 168 (0.52) | 209 (0.79) | 177 (0.49) |
| G/C | 290 (0.69) | 212 (0.48) | 203 (0.62) | 165 (0.63) | 180 (0.5) |

The data shows that in this experiment the second mismatches resulted in reduced mp values for the G/G homozygote (more non-specific HJ formation). Moreover, the discrimination between the heterozygotes and the G/G homozygote (the HET/HOM ratio shown in parentheses) did not improve significantly as compared with just one extra mismatch mm1.

It can be concluded that one extra mismatch immediately 5' of the SNP facilitates SNP detection in short amplicons, and a second mismatch at another position can also be introduced depending upon the amplicon.

6.5 Example 5

Addition of GC Clamp Greatly Increases HJ Formation in Short Amplicons

In order to determine the genotype at the site of SNP#4130 (NCBI dbSNP, ss#4130, shown below) for genomic DNA sample #1 of the M08PDR panel (Coriell Cell Repository, Camden, N.J.), target DNA with or without a GC clamp added at its 5' end was amplified by PCR using primer sets 4130F/(4130T1+4130T2) and 4130F2/(4130T1+4130T2) (shown below.)

Two template reference DNA with an introduced T→A mutation at the 3' of the polymorphic site were amplified by PCR using primer sets 4130ref-C/(4130T1+4130T2) and 4130ref-T/(4130T1+4130T2). Reference DNA were then amplified by a $2^{nd}$ round PCR using the two template reference DNA and primer sets 4130F/(4130T1+4130T2) and 4130F2/(4130T1+4130T2). PCR amplifications were carried out using a PTC-200 DNA Engine thermocycler (MJ Research Inc., Waltham, Mass.). 45 PCR cycles were performed with 10 s denaturation at 94° C., 15 s re-annealing at 58° C. and a 45 s extension at 72° C. The cycling was preceded by a 10-min incubation at 95°C. to activate AmpliTaq Gold™ DNA polymerase (Applied Biosystems, Foster City, Calif.).

Each target DNA was then mixed at 1:1 to each of the two reference DNA that were amplified using the same set of primers. For example, target DNA amplified using primer set 4130F/(4130T1+4130T2) was mixed with the two reference DNA amplified using primer set 4130F/(4130T1+4130T2). Each mixture was denatured at 95° C. for 2 minutes and followed by a 30-min incubation at 65° C. (re-annealing and branch migration). The reaction mixtures (100 ul) contained 10 ng genomic DNA, 2.5 U AmpliTaq Gold™ DNA polymerase, 200 mM each dNTP, 500 nM of the forward primer and 250 nM each of the reverse tailed primers in the BMB buffer (10 mM Tris-HCl, pH 8.3, 50 mM KCl, 4 mM MgCl2, 200 mg/ml BSA).

Genomic DNA sample #1 of the M08PDR panel is a C/C homozygote at SNPss#4130. As shown in FIG. 7, an extra-mismatch introduced at the 3' of the SNPss#4130 is not enough to cause significant Holliday Junction formation when the target DNA and the reference DNA have different genotype at the SNPss#4130, Addition of a GGGGCCCC clamp to the 5' end of the target and the reference DNA resulted in detectable Holliday Junctions when the target DNA and the reference DNA have different genotype at the SNPss#4130, In FIG. 7, lane 1 provides target DNA amplified using primer set 4130F/(4130T1+4130T2) mixed against reference C DNA amplified with primer set 4130F/(4130T1+4130T2). Lane 2 provides target DNA amplified using primer set 4130F/(4130T1+4130T2) mixed against reference T DNA amplified with primer set 4130F/(4130T1+4130T2). Lane 3 provides target DNA amplified using primer set 4130F2/(4130T1+4130T2) mixed against reference C DNA amplified with primer set 4130F2/(4130T1+4130T2). Lane 4 provides target DNA amplified using primer set 4130F2/(4130T1+4130T2) mixed against reference T DNA amplified with primer set 4130F2/(4130T1+4130T2).

SNPss#4130 has the following sequence: ttaa gtattacatg taaattaatc taaacttttt[C/T] ttgaat ccagtngtgt tttcagcaa gta (SEQ ID NO:37).

TABLE 3

Forward primers

| | | |
|---|---|---|
| F-1: | 5'-CACTTGGCAGATTTGAAGAGC-3' | (SEQ ID NO: 1) |
| F-2: | 5'-AAATAGTAGAAAGCGTGAGAGCACT-3' | (SEQ ID NO: 2) |
| 4129(A/T): | 5'-AAATAGTAGAAAGCGTGAGAGCACT(A/T)TTAGGA-3' | (SEQ ID NO: 3) |
| 4129(C/T): | 5'-AAATAGTAGAAAGCGTGAGAGCACT(C/T)TTAGGA-3' | (SEQ ID NO: 4) |
| 4129(A/C): | 5'-AAATAGTAGAAAGCGTGAGAGCACT(A/C)TTAGGA-3' | (SEQ ID NO: 5) |
| 4129(T/G): | 5'-AAATAGTAGAAAGCGTGAGAGCACT(T/G)TTAGGA-3' | (SEQ ID NO: 6) |
| 4129(A/G): | 5'-AAATAGTAGAAAGCGTGAGAGCACT(A/G)TTAGGA-3' | (SEQ ID NO: 7) |
| F-2(+2): | 5'-GCAAATAGTAGAAAGCGTGAGAGCACT-3' | (SEQ ID NO: 8) |
| F-2(+4): | 5'-AAGCAAATAGTAGAAAGCGTGAGAGCACT-3' | (SEQ ID NO: 9) |
| F-2(+6): | 5'-GGAAGCAAATAGTAGAAAGCGTGAGAGCACT-3' | (SEQ ID NO: 10) |
| F-2(+8): | 5'-GAGGAAGCAAATAGTAGAAAGCGTGAGAGCACT-3' | (SEQ ID NO: 11) |
| F-2(+10): | 5'-AAGAGGAAGCAAATAGTAGAAAGCGTGAGAGCACT-3' | (SEQ ID NO: 12) |
| 4129(A): | 5'-AAATAGTAGAAAGCGTGAGAGCACTATTAGGA-3' | (SEQ ID NO: 13) |
| 4129(T): | 5'-AAATAGTAGAAAGCGTGAGAGCACTTTTAGGA-3' | (SEQ ID NO: 14) |
| 4129(G): | 5'-AAATAGTAGAAAGCGTGAGAGCACTGTTAGGA-3' | (SEQ ID NO: 15) |
| 4129(C): | 5'-AAATAGTAGAAAGCGTGAGAGCACTCTTAGGA-3' | (SEQ ID NO: 16) |
| F-2(A)mm1: | 5'-AAATAGTAGAAAGCGTGAGAGCACAATTAG-3' | (SEQ ID NO: 17) |
| F-2(G)mm1: | 5'-AAATAGTAGAAAGCGTGAGAGCACAGTTAG-3' | (SEQ ID NO: 18) |
| F-2(A)mm1 + 2: | 5'-AAATAGTAGAAAGCGTGAGTGCACAATTAG-3' | (SEQ ID NO: 19) |
| F-2(G)mm1 + 2: | 5'-AAATAGTAGAAAGCGTGAGTGCACAGTTAG-3' | (SEQ ID NO: 20) |
| F-2(A)mm1 + 3: | 5'-AAATAGTAGAAAGCGAGAGAGCACAATTAG-3' | (SEQ ID NO: 21) |
| F-2(G)mm1 + 3: | 5'-AAATAGTAGAAAGCGAGAGAGCACAGTTAG-3' | (SEQ ID NO: 22) |
| F-2(A)mm1 + 4: | 5'-AAATAGTAGAATGCGTGAGAGCACAATTAG-3' | (SEQ ID NO: 23) |
| F-2(G)mm1 + 4: | 5'-AAATAGTAGAATGCGTGAGAGCACAGTTAG-3' | (SEQ ID NO: 24) |
| F-2(A)mm1 + 5: | 5'-AAATAGTTGAAAGCGTGAGAGCACAATTAG-3' | (SEQ ID NO: 25) |
| F-2(G)mm1 + 5: | 5'-AAATAGTTGAAAGCGTGAGAGCACAGTTAG-3' | (SEQ ID NO: 26) |
| F-2(A)mm1 + 6: | 5'-AAATAGTAGAAAGCGTGAGAGCACAAATAG-3' | (SEQ ID NO: 27) |
| F-2(G)mm1 + 6: | 5'-AAATAGTAGAAAGCGTGAGAGCACAGATAG-3' | (SEQ ID NO: 28) |

TABLE 4

Reverse Tailed primers

| | | |
|---|---|---|
| T1-1: | 5'-*ACCATGCTCGAGATTACGAGT*CACAAATTACGTGAGAAACCG-3' | (SEQ ID NO: 29) |
| T2-1: | 5'-*GATCCTAGGCCTCACGTATTT*CACAAATTACGTGAGAAACCG-3' | (SEQ ID NO: 30) |
| T1-2: | 5'-*ACCATGCTCGAGATTACGAG*AAATGCCAATCCCTGTCCTAA-3' | (SEQ ID NO: 31) |
| T2-2: | 5'-*GATCCTAGGCCTCACGTATT*AAATGCCAATCCCTGTCCTAA-3' | (SEQ ID NO: 32) |
| T1-3: | 5'-*ACCATGCTCGAGATTACGAG*GGAAATGCCAATCCCTGT-3' | (SEQ ID NO: 33) |
| T2-3: | 5'-*GATCCTAGGCCTCACGTATT*GGAAATGCCAATCCCTGT-3' | (SEQ ID NO: 34) |
| T1-4: | 5'-*ACCATGCTCGAGATTACGAGT*AAGGGGAAATGCCAATC-3' | (SEQ ID NO: 35) |
| T2-4: | 5'-*GATCCTAGGCCTCACGTATTT*AAGGGGAAATGCCAATC-3' | (SEQ ID NO: 36) |

| Primers (Example 5) | | |
|---|---|---|
| 4130F: | <u>TTAAGTATTACATGTAAATTAATCTAAACTTTT</u><br>(33 mer, Tm=63.6° C., with no GC clamp) | (SEQ ID NO: 38) |
| 4130F2: | GGGGCCCC<u>TTAAGTATTACATGTAAATTAATCTAAACTTTT</u><br>(41 mer, Tm=77.0° C., with a GC clamp) | (SEQ ID NO: 39) |
| 4130ref-C: | AGTATTACATGTAAATTAATCTAAACTTTTCATGAAT<br>(37 mer, introduced A→T mismatch at the 3' of the SNP) | (SEQ ID NO: 40) |
| 4130ref-T: | AGTATTACATGTAAATTAATCTAAACTTTTTATGAAT<br>(37 mer, introduced A→T mismatch at the 3' of the SNP) | (SEQ ID NO: 41) |
| 4130T1: | <u>ACCATGGTCACGATTACGAG</u>TACTTGCTGCAAACACGACTGGATTCA | (SEQ ID NO: 42) |
| 4130T2: | <u>GATCCTAGGCCTCACTGTTA</u>TACTTGCTGCAAACACGACTGGATTCA | (SEQ ID NO: 43) |

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended set forth below.

All references cited herein are hereby incorporated by reference in their entireties.

What is claimed is:

1. A method for determining the genotype at the site of a polymorphism in a target polynucleotide sequence comprising:

a) contacting a first partial duplex comprising a target polynucleotide sequence with a second partial duplex comprising a mutated reference polynucleotide sequence under conditions in which said first and said second partial duplexes form a four-way complex, wherein said mutated reference polynucleotide is designed to be identical to a reference polynucleotide everywhere except at the site of a mutation that is not at the site of the polymorphism, and wherein said reference polynucleotide sequence corresponds to said target polynucleotide sequence and has a known genotype at the site of the polymorphism;

b) subjecting said four-way complex to branch migration conditions, wherein branch migration in said four-way complex is impeded at or near the site of the polymorphism if the target polynucleotide sequence has a genotype at the site of the polymorphism that differs from that of the reference polynucleotide sequence, thereby forming a stabilized four-way complex, and wherein branch migration in the four-way complex is capable of continuing until complete strand exchange occurs if the target polynucleotide sequence and the reference polynucleotide sequence share the same genotype at the site of the polymorphism, thereby resulting in the resolution of said four-way complex into two duplex nucleic acids; and c) detecting said stabilized four-way complex as an indication that said target polynucleotide sequence has a genotype that is different from the known genotype of said reference polynucleotide sequence at said site of the polymorphism, or detecting resolution of said four-way complex into two duplex nucleic acids as an indication that said target polynucleotide sequence has a genotype that is the same as the known genotype of said reference polynucleotide sequence at said site of the polymorphism.

2. The method of claim 1, wherein said mutated reference polynucleotide sequence and said target polynucleotide sequence differ at the site of the mutation.

3. The method of claim 2, wherein said mutation is a single-base mutation.

4. The method of claim 2, wherein said mutation is a multiple-base mutation or a mutation that comprises multiple single-base mutations.

5. The method of claim 1, wherein said mutation is less than 20 nucleotides away from said site of the polymorphism.

6. The method of claim 5, wherein said mutation is 4, 3, or 2 nucleotides away from said site of the polymorphism or adjacent to the site of the polymorphism.

7. The method of claim 6, wherein said mutation is 5' of said site of the polymorphism and adjacent to said site of the polymorphism.

8. The method of claim 6, wherein said mutation is 3' of said site of the polymorphism and adjacent to said site of the polymorphism.

9. The method of claim 1, wherein said first and said second partial duplexes comprise GC-rich sequences.

10. The method of claim 1, wherein said first and said second partial duplexes comprise minor groove binding motifs.

11. The method of claim 1, wherein said first and second partial duplexes comprise nucleic acid modifications or peptide nucleic acid backbones.

12. A method for determining the genotype at the site of a polymorphism in a target polynucleotide sequence comprising:

a) contacting a first partial duplex comprising a mutated target polynucleotide sequence with a second partial duplex comprising a reference polynucleotide sequence, wherein said mutated target polynucleotide sequence is designed to be identical to a target polynucleotide sequence everywhere except at the site of a mutation that is not at the site of the polymorphism, and wherein said reference polynucleotide sequence corresponds to said target polynucleotide sequence and has a known genotype at the site of the polymorphism;

b) subjecting said four-way complex to branch migration conditions, wherein branch migration in said four-way complex is impeded at or near the site of the polymorphism if the target polynucleotide sequence has a genotype at the site of the polymorphism that differs from that of the reference polynucleotide sequence, thereby forming a stabilized four-way complex, and wherein branch migration in the four-way complex is capable of continuing until complete strand exchange occurs if the target polynucleotide sequence and the reference polynucleotide sequence share the same genotype at the site of the polymorphism, thereby resulting in the resolution of said four-way complex into two duplex nucleic acids; and c) detecting said stabilized four-way complex as an indication that said target polynucleotide sequence has a genotype that is different from the known genotype of said reference polynucleotide sequence at said site of the polymorphism, or detecting resolution of said four-way complex into two duplex nucleic acids as an indication that said target polynucleotide sequence has a genotype that is the same as the known genotype of said reference polynucleotide sequence at said site of the polymorphism.

13. The method of claim 12, wherein said mutated target polynucleotide sequence and said reference polynucleotide sequence differ at the site of the mutation.

14. The method of claim 13, wherein said mutation is a single-base mutation.

15. The method of claim 13, wherein said mutation is a multiple-base mutation or a mutation that comprises multiple single-base mutations.

16. The method of claim 13, wherein said mutation is less than 20 nucleotides away from said site of the polymorphism.

17. The method of claim 16, wherein said mutation is 4, 3, or 2 nucleotides away from said site of the polymorphism or adjacent to said site of the polymorphism.

18. The method of claim 17, wherein said mutation is 5' of said site of the polymorphism and adjacent to said site of the polymorphism.

19. The method of claim 17, wherein said mutation is 3' of said site of the polymorphism and adjacent to said site of the polymorphism.

20. The method of claim 12, wherein said first and said second partial duplexes comprise GC-rich sequences.

21. The method of claim 12, wherein said first and said second partial duplexes comprise minor groove binding motifs.

22. The method of claim 12, wherein said first and said second partial duplexes comprise nucleic acid modifications or peptide nucleic acid backbones.

* * * * *